(12) United States Patent
Cheng et al.

(10) Patent No.: US 7,709,664 B2
(45) Date of Patent: May 4, 2010

(54) COUMARIN DERIVATIVES USEFUL AS TNFα INHIBITORS

(75) Inventors: Jie Fei Cheng, Carlsbad, CA (US); Thomas Arrhenius, Del Mar, CA (US); David Wallace, San Diego, CA (US); Mi Chen, San Diego, CA (US); Sovouthy Tith, San Diego, CA (US); Hirotaka Kashiwagi, Shizuoka (JP); Yoshiyuki Ono, Shizuoka (JP); Yoshiaki Watanabe, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 1183 days.

(21) Appl. No.: 11/225,940

(22) Filed: Sep. 13, 2005

(65) Prior Publication Data
US 2006/0020138 A1    Jan. 26, 2006

Related U.S. Application Data

(62) Division of application No. 10/333,366, filed as application No. PCT/US01/22950 on Jul. 19, 2001, now Pat. No. 7,026,491.

(60) Provisional application No. 60/220,048, filed on Jul. 21, 2000, provisional application No. 60/225,448, filed on Aug. 14, 2000, provisional application No. 60/303,030, filed on Jul. 3, 2001.

(51) Int. Cl.
*C07D 311/12* (2006.01)
(52) U.S. Cl. .................................. 549/289
(58) Field of Classification Search ............ 549/289
See application file for complete search history.

(56) References Cited

U.S. PATENT DOCUMENTS 3,259,635 A    7/1966    Ritter et al.

FOREIGN PATENT DOCUMENTS

| CH | 522 631 A | 6/1972 |
|---|---|---|
| EP | 0 171 645 | 2/1986 |
| EP | 0 428 939 | 5/1991 |
| WO | WO 92/11383 | 7/1992 |
| WO | WO 99/15523 | 4/1999 |

OTHER PUBLICATIONS

Chem. Abst. 130:90514, RN 219552-31-5, Feb. 10, 1999.*
Chem. Abst. 30:7964, RN 109650-11-5, Aug. 8, 1987.*
Chem. Abst. 70:119995, RN 23368-41-4, Nov. 16, 1984.*
Chem. Abst. 61:47737, RN 93655-49-3, Dec. 18, 1984.*
Chem. Abst. 47:2642, RN 86-44-2, Nov. 16, 1984.*
Chemical Abstracts, Registry No. 93876-51-8 (1984).*
Beutler et al., Science, Oct. 1986, pp. 470-474, vol. 234.
Grilli et al., International Review of Cytology, 1993, pp. 1-63, vol. 143.
Pisetsky, The New England Journal of Medicine, Mar. 2000, pp. 810-811, vol. 342, No. 11.
Shohami et al., Journal of Cerebral Blood Flow and Metabolism, 1994, pp. 615-619, vol. 14, No. 4.
Van Dullemen et al., Gastroenterology, 1995, pp. 129-135, vol. 109, No. 1.

* cited by examiner

*Primary Examiner*—Bernard Dentz
(74) *Attorney, Agent, or Firm*—Fish & Richardson P.C.

(57) ABSTRACT

Novel compounds composition capable of inhibiting TNFα and having anti immunoinflammatory and autoimmune properties useful in a pharmaceutical composition, such as for a drug containing this as an active ingredient; and a therapeutic method with the use of these novel compounds.

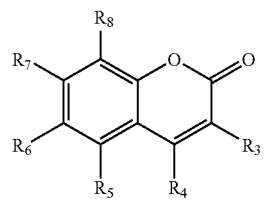

2 Claims, No Drawings

COUMARIN DERIVATIVES USEFUL AS TNFα INHIBITORS

RELATED APPLICATIONS

The present application is a divisional application of U.S. Ser. No. 10/333,366, filed Jun. 6, 2003, now U.S. Pat. No. 7,026,491 as a National Stage of International Patent Application PCT/US01/22950, filed Jul. 19, 2001, which claims priority to U.S. Provisional Patent Application Ser. Nos. 60/220,048, filed Jul. 21, 2000; 60/225,448, filed Aug. 14, 2000; and 60/303,030, filed Jul. 3, 2001, respectively. The contents of these prior applications are incorporated herein by reference in their entirety.

FIELD OF THE INVENTION

This invention relates to novel coumarin compounds and their pharmaceutically acceptable salts, pharmaceutical compositions containing such compounds and the use of such compounds as TNFα inhibitors.

BACKGROUND

Tumor Necrosis Factor alpha or TNFα, is a pro-inflammatory cytokine secreted by a variety of cells, including monocytes and macrophages, in response to many inflammatory stimuli or external cellular stress. It is a key cytokine in the inflammation cascade causing the production and/or release of other cytokines and agents.

Excessive or unregulated TNFα production has been implicated in mediating or exacerbating a number of disease states. Decreasing TNFα levels thus constitutes a valuable therapeutic strategy for the treatment of many inflammatory, infectious, immunological or malignant diseases. Collectively such disorders may be grouped as "immunoinflammatory maladies." These "immunoinflammatory maladies" include, but are not restricted to rheumatoid arthritis, Paget's disease, osteoporosis, multiple myeloma, uveititis, acute and chronic myelogenous leukemia, pancreatic β cell destruction, rheumatoid spondylitis, gouty arthritis, inflammatory bowel disease, adult respiratory distress syndrome (ARDS), psoriasis, Crohn's disease, allergic rhinitis, ulcerative colitis, anaphylaxis, asthma, muscle degeneration, cachexia, Reiter's syndrome, type I and type II diabetes, bone resorption diseases, graft vs. host reaction, ischemia reperfusion injury, atherosclerosis, brain trauma, multiple sclerosis, cerebral malaria, sepsis, septic shock, toxic shock syndrome, fever, and malgias due to infection.

TNFα appears to be involved in bone resorption diseases, including arthritis. In rheumatoid arthritis, TNFα induce synoviocytes and chondrocytes to produce collagenase and neutral proteases, which leads to tissue destruction within the arthritic joints.

It has been reported that TNFα plays a role in head trauma, stroke and ischemia. The TNFα levels increased in the contused hemisphere in rat models of head trauma (Shohami et al., *J. Cereb. Boold Flow Metab.* 14, 615(1994)).

TNFα also plays a role in the area of chronic pulmonary inflammatory diseases. The deposition of silica particles leads to silicosis, a disease of progressive respiration failure caused by a fibrotic reaction.

TNFα blockage has been shown to be beneficial in rheumatoid arthritis and other diseases (Elliot et al., *Int. J. Pharmac.* 17(2), 141 (1995), Pisetsky, *N. Engl. J. Med.* 342(11), 810-1(2000)). Several approaches have been taken to block the effect of TNFα. One approach involves using soluble receptors for TNFα, which have demonstrated efficacy in animal models of TNFα mediated disease states. Enbrel®, a solublized TNFα receptor, has shown efficacy against moderately to severely active rheumatoid arthritis and has been approved for use in those patients who have an inadequate response to one or more disease-modifying anti-rheumatic drugs. A second approach is to neutralize TNFα using a monoclonal antibody specific to TNFα. For instance, a TNFα-binding chimerical monoclonal antibody, Remicade™, has demonstrated improvement in swollen joint count in a human trial of rheumatoid arthritis and marked in conjunction with methotrexate for the treatment of patients with rheumatoid arthritis who have had an inadequate response to methotrexate alone. Suppression of the effects of TNFα has also been achieved through the utilization of steroids such as dexamethasone and prednisolone in the early experiments (Beutler et al., *Science* 234, 470474 (198-5); WO 92/11383).

High levels of TNFα are associated with Crohn's disease (von Dullemen et al., *Gastroenterology* 109, 129 (1995)) and clinical benefit has been achieved with TNFα antibody treatment. The TNFα-binding chimerical monoclonal antibody, Remicade™, has also been approved for use in treatment of Crohn's disease patients.

The transcription factor Nuclear Factor kB (NFkB) has been shown to regulate the production of many proinflammatory cytokines including but not limited TNFα and related proteins that are elevated in immunoinflammatory diseases (Grilli et al., *Int. Rev. Cytol.* 143, 1-62(1993)). The TNFα level and transcription activity of NFkB are influenced by a reciprocal feedback loop. The compounds described in this invention affect both the TNFα level and transcription activity of NFkB. NFkB has been shown to play a role in diseases including osteoarthritis, transplant rejection, ischemia, reperfusion injury, trauma, certain cancers and viral disorders, and autoimmune diseases such as rheumatoid arthritis, multiple sclerosis, psoriasis, inflammatory bowel disease, glomerulonephritis, lupus and juvenile diabetes.

SUMMARY OF THE INVENTION

This invention relates to the use of TNFα inhibiting compounds and compositions, which have an anti-immunoinflammatory effect, and thus are useful in treating immunoinflammatory maladies, and as such are useful in treating, among other things, autoimmune diseases.

In relation to these uses, this invention relates to novel compounds of Formula (I) (Compound (I)), and compositions thereof, useful in the prevention and treatment of immunoinflammatory and autoimmune diseases by inhibition of TNFα. The compounds disclosed have the following general structure (Formula (I))

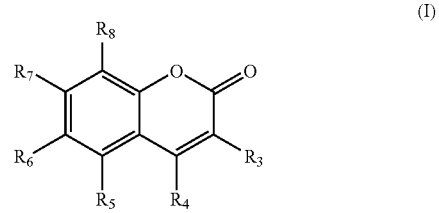

as defined in the following claims, as well as their pharmaceutical compositions and the uses of these compounds both to prepare medicaments generally and for the preferred uses as treatments.

DETAILED DESCRIPTION OF THE INVENTION

Without being limited by the theory, it is thought that the compounds of this invention decrease the TNFα blood levels, and thus have utility as antiinflammatory agents in general and in the prevention and/or treatment of a variety of conditions, including but not limited to immunoinflammatory and autoimmune diseases.

Preferred compounds of this invention are generally represented by the following general structure (I):

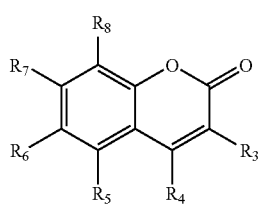

wherein R₃ is referred to as an aryl methylene group.

Preferred compounds of this invention include compounds of formula (I) wherein R₇ is selected from:

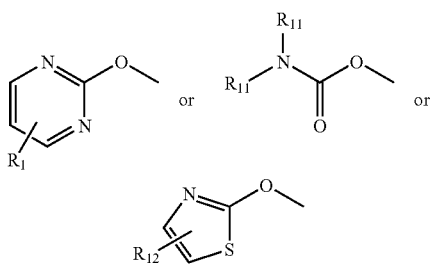

As used herein, "Ar" means aryl. "Aryl" means a substituted or unsubstituted radical consisting of an aromatic ring, which may or may not include one or more heteroatoms. Hence the term "heteroaryl" is clearly contemplated in the term "aryl". Preferred are monocyclic heterocycles of 5 or 6 members or bicyclic heterocycles 8 to 10 members. Preferably where the term aryl represents a six membered heterocycle, the heteroatom(s) are from one to three N atoms, and preferably wherein when "aryl" is a heterocycle of five members, it has one or two heteroatoms selected from O, N, or S. When "aryl" is bicyclic, preferably it is an eight to ten membered bicyclic. Preferably if the bicyclic aryl is a heterocycle, the heteroatom(s) are from one to three N atoms, or one to three heteroatoms selected from O, N, or S. Hence, preferred heterocycles have up to three heteroatoms are present in the aromatic ring. The skilled artisan will recognize that among aryl with heteroatoms included in the aromatic ring, there are both five and six membered rings. Examples of monocyclic "aryl" include; phenyl, thienyl, pyridyl, pyrimidyl, pyridazyl, furyl, oxazolyl, imidazolyl, thiazolyl, oxadiazilyl, triazinyl, triazolyl, thiadiazolyl, and others, which the skilled artisan will recognize. Examples of monocyclic "aryl" include benzofuranyl, benzimidizolyl, pyridazofuranyl, pyridopyranyl, pyridoimidizolyl and the like. Such aryl rings can be connected to the benzopyrane moiety via any carbon or any available valance on the ring. The most preferred aryl rings include phenyl, pyridyl, furyl, or thienyl.

In this definition it is clearly contemplated that substitution on the aryl ring is within the scope of this invention. Where substitution occurs, the radical is called substituted aryl. Preferably one to three, more preferably one or two, and most preferably one substituent occurs on the aryl ring. Preferred substitution patterns in six membered rings are "meta" substituents, that is they are substituted in the 3 position relative to the connection to the benzopyrane. Preferred substitution patterns in five membered rings are substituted in the 2 position relative to the connection to the benzopyrane. Though many substituents will be useful, preferred substituents include carbamates, ureas, sulfonamides, esters, amides, and the like.

As used herein, "alkoxy" means a substituent having the structure R—O—, where R is linear or branched alkanyl or alkenyl. As used herein, "alkanyl" means a saturated hydrocarbon radical substituent, straight, cyclic or branched chain, unsubstituted or substituted. As used herein, "alkenyl" means a hydrocarbon substituent with one double bond, straight or branched chain.

As used herein, "alkyl" means a hydrocarbon substituent, which is linear or branched alkanyl or alkenyl. Preferred alkyls are of 1 to about 5 carbons, More preferred alkyls are $C_1$ to about $C_4$ substituents, and most preferred are $C_1$ to $C_4$ alkyl.

As used herein, "alkylene" means a hydrocarbon diradical, which is linear or branched alkanyl or alkenyl. Preferred alkyls are of 1 to about 5 carbons, More preferred alkyls are $C_1$ to about $C_4$ substituents, and most preferred are $C_1$ to $C_4$ alkyl. Examples of such alkylenes, include methylene, ethylene, and the like, such diradicals may act as spacers between radicals, other atoms, or between the parent ring and another functional group.

"Halo" is a chloro, bromo, fluoro or iodo atom radical. Chloro and fluoro are preferred halides, the term halo also contemplates terms sometimes referred to as "halogen", or "halide".

As used herein, "haloalkyl" means a hydrocarbon substituent, which is linear or branched alkanyl or alkenyl, substiuted with chloro, bromo, fluoro or iodo atom(s). Most preferred of these are fluoroalkyls, wherein one or more of the hydrogen atoms have been substituted by fluoro. Preferred haloalkyls are of 1 to about 5 carbons in length, More preferred haloalkyls are $C_1$ to about $C_4$ substituents, and most preferred are $C_1$ to $C_3$ subsituents. The skilled artisan will recognize, then that as used herein, "haloalkylene" means a diradical variant of haloalkyl, such diradicals may act as spacers between radicals, other atoms, or between the parent ring and another functional group.

"Heterocyclyl" includes radical heterocycles which are saturated, unsaturated, and aromatic. These may be substituted or unsubstituted, and are attached to other radicals or the benzopyrane ring via any available valence, preferably any available carbon. Hence this definition contemplated such radicals as heterocyclyl, hetercyclyloxy, and the like. More preferred heterocycles are of 5 or 6 members. In six membered aromatic monocyclic heterocycles, the heteroatom(s)

are from one to three Ns, and wherein when the heterocycle is five membered and aromatic, preferably it has one or two heteroatoms selected from O, N, or S. However, heterocyclyl does not require that the heterocycle is aromatic or unsaturated, it may be saturated or unsaturated or aromaitc, such as morpholino, piperidino, pyranonyl, benzimidazolyl, benzofuranyl, oxalolidinyl, oxazolyl, or the like.

"Substituted phenyl" or "substituted aryl" represents any phenyl or other aryl radical, which has one or more substitutions on any of the remaining positions on the ring. The skilled artisan knows suitable substitutions, and methods to prepare substituted phenyls and aryls would be known in the art, and are available through standard sources. See for example, March *Advanced Organic Chemistry* (Wiley), Carey and Sundberg *Advanced Organic Chemistry* (vol. 2) and the like.

Certain radicals are not further defined here. The skilled artisan, armed with the knowledge of IUPAC methods of nomenclature is well aware of the meaning of radicals named by this well accepted method. Hence, it is clear that hydroxyethlyene refers to HOCH2CH2-, methylcarbonyl refers to CH3CO—. It is also apparent that certain radicals are generally referred to by common names, which are known in the art. Hence, the skilled artisan will recognize that CH3CO— is also refers to acetyl, HCO— is referred to as formyl, and other examples can be cited here, but are not for the sake of space.

Compounds and compositions herein also specifically contemplate pharmaceutically acceptable salts, whether cationic or anionic. A "pharmaceutically-acceptable salt" is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987 (incorporated by reference herein). Preferred salts formable at acidic groups can include cations, such as the alkali metal salts (such as sodium and potassium), and alkaline earth metal salts (such as magnesium and calcium) and organic salts. Preferred salts formable at basic sites include anions such as the halides (such as chloride salts). Of course, the skilled artisan is aware that a great number and variation of salts may be used, and examples exist in the literature of both organic or inorganic salts useful in this manner.

It is also clearly contemplated that compounds of the invention can be provided as biohydrolyzable prodrugs, as they are understood in the art. These include for example, biohydrolyzable amides and esters. "Biohydrolyzable amide" is an amide of a compound which does not essentially interfere with the activity of the compound, or that is readily converted in vivo by a human or lower animal subject to yield an active of the invention. A "biohydrolyzable ester" refers to an ester of the compound of the invention that does not interfere with the activity of these compounds or that is readily converted by an animal to yield an active Formula (I) compound. Such biohydrolyzable prodrugs are understood by the skilled artisan and are embodied in regulatory guidelines.

Inasmuch as the compounds of the invention may contain optical centers, "Optical isomer", "stereoisomer", "enantiomer," "diastereomer," as referred to herein have the standard art recognized meanings (Cf., *Hawleys Condensed Chemical Dictionary*, 11th Ed.) and are included in the compounds claimed, whether as racemates, or their optical isomers, stereoisomers, enantiomers, diastereomers.

The illustration of specific protected forms and other derivatives of the Formula (I) compounds is not intended to be limiting. The application of other useful protecting groups, salt forms, etc. is within the ability of the skilled artisan.

Where nomenclature is simple, for the purposes of nomenclature the numbering follows the IUPAC convention. For illustration purposes, the parent benzopyrane ring structure is IUPAC numbered as follows:

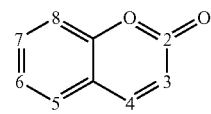

Preparation of the Compounds of the Invention

The starting materials used in preparing the compounds of the invention are known, made by known methods, or are commercially available as a starting material. It will be apparent to the skilled artisan that methods for preparing precursors and functionality related to the compounds claimed herein are generally described in the literature. The skilled artisan given the literature and this disclosure is well equipped to prepare any of the claimed compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as March *Advanced Organic Chemistry* (Wiley), Carey and Sundberg, *Advanced Organic Chemistry* and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene *Protecting Groups in Organic Synthesis*.

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure.

Note that in these schemes the term "aryl methylene" is used for $R_3$ by example. The skilled artisan will recognize that $R_3$, as defined, includes this preferred moiety, and all $R_3$ radicals are obtainable by these methods.

Scheme 1

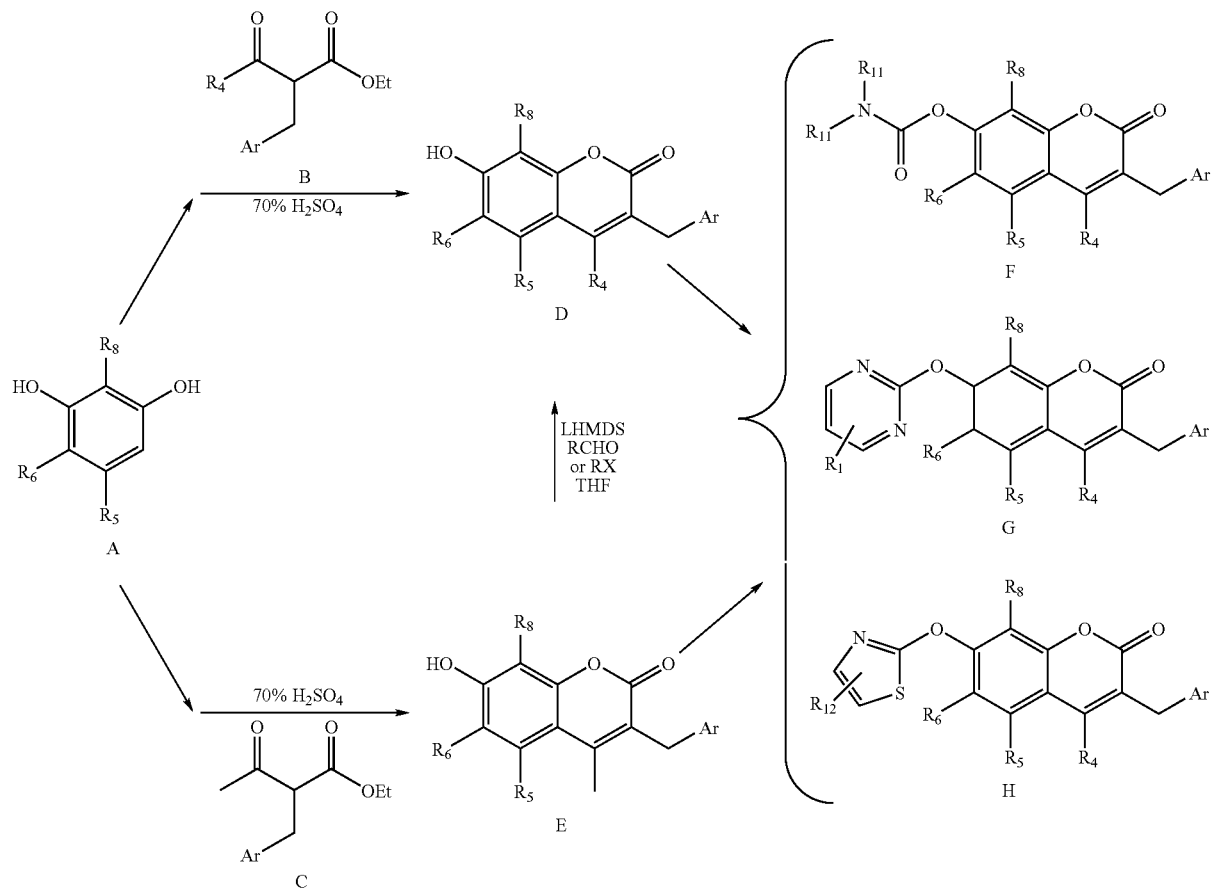

The C-7 hydroxyl coumarin compounds (D and E) are prepared from resorcinol or substituted resorcinol (A) and p-ketoesters (B or C) according to the published procedures (Usgaonkar et al., *J. Indian Chem. Soc.* 30, 743 (1953)). Thus, 2-arylmethyl β-ketoesters (B) react with resorcinol or substituted resorcinol in 70% sulfuric acid to furnish 3-arylmethyl-4-substituted coumarins (D). Alternatively, they can be prepared through C-4 alkylation of 3-arylmethyl-4-methyl coumarins (E), which are in turn prepared from 2-arylmethyl acetoacetates (C) with resorcinol derivatives, under the conditions depicted in Scheme 1. Upon treatment with NaH, or other appropriate reagent, and appropriate halides (such as carbamoyl chlorides, 2-halopyrimidines and 2-halothiazoles), these two C-7 hydroxy coumarin intermediates (D and E) are converted into the desired C-7 carbamates (F), oxypyrimidine (G) and oxythiazole (H) derivatives as shown in Scheme 1.

Scheme 2

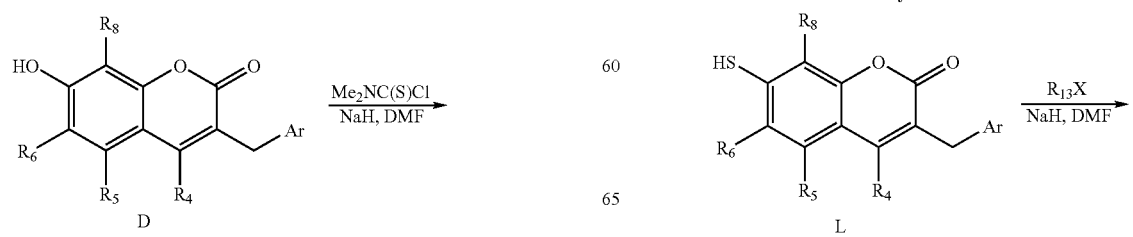

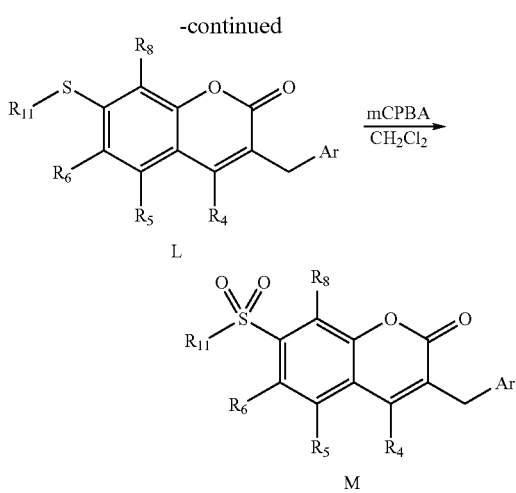

The C-7 hydroxyl intermediates D or E (Scheme 1) are also used to prepare C-7 thio-containing derivatives according to Scheme 2. Under similar conditions, C-7 hydroxyl compounds D react with thiocarbamoyl chloride to afford the thiocarbamic acid O-esters (i). These thiocarbamic acid O-esters are rearranged into C-7 thiocarbamic acid S-ester derivatives (J) upon refluxing in diphenylether. Further elaboration on C-7 thiol intermediates (K), which are obtained through hydrolysis of thiocarbamate (4), furnishes the corresponding aliphatic or aromatic sulfides (L), sulfoxides or sulfones (M).

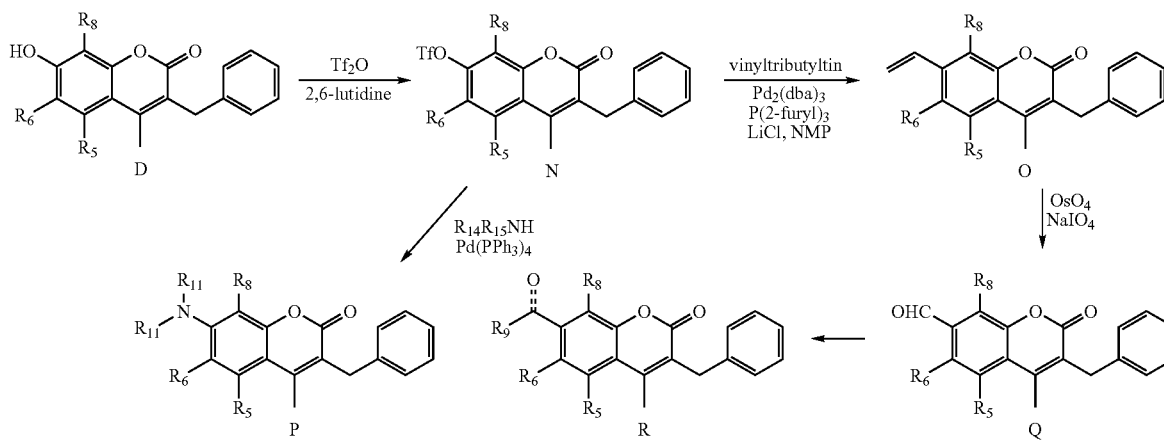

3-Benzyl-4-methyl C-7 triflates (N), prepared from the corresponding C-7 hydroxyl coumarin C (Scheme 1) under conventional conditions, are subjected into Still coupling (*Organic Reactions* 50, 1 (1997)) to afford the alkylated derivatives O or into directly amination (Wolfe and Buchwald, *J. Org. Chem.* 62, 1264 (1997)) to afford amino derivatives (P). The intermediates O are then transformed into other derivative (R) which contain different groups at C-7 position via aldehyde intermediates (O).

Compositions

The pharmaceutical compositions containing Compound (I) can be administered either orally or parentally, though oral administration thereof is preferred. These pharmaceutical compositions may be in dosage forms appropriate for the administration routes.

Pharmaceutical compositions containing Compound (I) as an active ingredient are formulated by techniques commonly employed in the art. Namely, these compositions are prepared as solids and liquids, such as tablets, capsules, granules, powders, syrups, injections and ointments depending on the purpose, or route of administration. In formulation, solid or liquid carriers or fillers, commonly employed in the art are used.

The amount of Compound (I) in these preparations varies depending on the dosage form. It is generally preferable that these preparations contain from 0.00001 to 20% by weight of Compound (I). The dose of the compositions of this invention may be varied over a wide range depending on the type of the warm-blooded animal (for example, mammals, and more preferably humans) to be treated, the severity of the symptoms, a doctor's diagnosis, etc. In general, the daily dose thereof, in terms of an active ingredient, ranges from 0.0001 to 1 g/kg in the case of oral administration or from 0.00001 to 10 mg/kg in the case of parenteral administration. The administration in the dose as specified above may be made once to several times per 1 to 30 days and the administration schedule may be appropriately varied depending on the severity of the symptoms or in accordance with a doctor's judgement.

Preferred compositions of this invention include solids, such as tablets and capsules, and liquids, such as solutions, suspensions and emulsions (preferably in soft gelatin capsules), comprising a safe and effective amount of a subject compound intended for topical administration to the gastrointestinal tract by peroral administration. Such compositions preferably comprise from about 0.01 mg to about 100 mg per dose, more preferably from about 0.1 mg to about 50 mg per dose. Such compositions can be coated by conventional methods, typically with pH or time-dependent coatings, such that the subject compound is released in the gastrointestinal tract in the vicinity of the desired topical application, or at various times to extend the desired action.

Another aspect of this invention is compositions which comprise a safe and effective amount of a subject compound, or a pharmaceutically-acceptable salt thereof, and a pharmaceutically-acceptable carrier. As used herein, "safe and effective amount" means an amount of the subject compound sufficient to significantly induce a positive modification in the condition to be treated, but low enough to avoid serious side effects (at a reasonable benefit/risk ratio), within the scope of sound medical judgement. A safe and effective amount of the subject compound will vary with the age and physical condition of the patient being treated, the severity of the condition, the duration of the treatment, the nature of concurrent therapy, the particular pharmaceutically-acceptable carrier utilized, and like factors within the knowledge and expertise of the attending physician.

Compositions of this invention preferably comprise from about 0.0001% to about 99% by weight of the subject compound, more preferably from about 0.01% to about 90%; also preferably from about 10% to about 50%, also preferably from about 5% to about 10%, also preferably from about 1% to about 5%, and also preferably from about 0.1% to about 1%.

In addition to the subject compound, the compositions of this invention contain a pharmaceutically-acceptable carrier. The term "pharmaceutically acceptable carrier", as used herein, means one or more compatible solid or liquid filler diluents or encapsulating substances which are suitable for administration to a human or lower animal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the human or lower animal being treated.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4.

The preferred mode of administering the subject compounds is perorally. The preferred unit dosage form is therefore tablets, capsules, lozenges, chewable tablets, and the like. Such unit dosage forms comprise a safe and effective amount of the subject compound, which is preferably from about 0.01 mg to about 200 mg, more preferably from about 0.1 mg to about 50 mg, more preferably still from about D0.5 mg to about 25 mg, also preferably from about 1 mg to about 10 mg. The pharmaceutically-acceptable carrier suitable for the preparation of unit dosage forms for peroral administration are well-known in the art.

Peroral compositions also include liquid solutions, emulsions, suspensions, and the like. The pharmaceutically-acceptable carriers suitable for preparation of such compositions are well known in the art. Such liquid oral compositions preferably comprise from about 0.001% to about 5% of the subject compound, more preferably from about 0.01% to about 0.5%.

Other compositions useful for attaining systemic delivery of the subject compounds include sublingual and buccal dosage forms. Such compositions typically comprise soluble filler substances; and binders, as well as optional glidants, lubricants, sweeteners, colorants, antioxidants and flavoring agents disclosed above may also be included.

Preferred compositions of this invention include aqueous solutions comprising a safe and effective amount of a subject compound intended for topical (including ocular or intranasal) administration. Such preferred compositions of this invention include aqueous solutions, suspensions, and dry powders comprising a safe and effective amount of a subject compound which can be administered in a variety of ways, including atomisation and topical inhalation administration. Such compositions preferably comprise from about 0.1% to about 50% of a subject compound, more preferably from about 1% to about 20%. Such compositions are typically contained in a container with attached atomising means. Such compositions also typically include propellants: solvents; stabilisers, preservatives; toxicity adjusters, buffers; and antioxidants. Acids and bases may be used to adjust the pH of these formulations as needed.

EXAMPLES

To further illustrate this invention, the following examples are included. The examples should not, of course, be construed as specifically limiting the invention. Variations of these examples within the scope of the claims are within the purview of one skilled in the art are considered to fall within the scope of the invention as described, and claimed herein. The reader will recognize that the skilled artisan, armed with the present disclosure, and skill in the art is able to prepare and use the invention without exhaustive examples.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

$^1$H nuclear magnetic resonance spectra (NMR) is measured in $CDCl_3$ or other solvents as indicated by a Varian NMR spectrometer (Unity Plus 400, 400 MHz for $^1$H) unless otherwise indicated and peak positions are expressed in parts per million (ppm) downfield from tetramethylsilane. The peak shapes are denoted as follows, s, singlet; d, doublet; t, triplet; m, multiplet.

The following abbreviations have the indicated meanings.
Ac=acetyl
Bn=benzyl
$CDCl_3$=deutered chloroform
$CD_3OD$=deutered methanol
$CH_2Cl_2$=dichloromethane
CuCl=copper (I) chloride
CuCN=copper (I) cyanide
DAST=diethylaminosulfur trifluodride.
DIBAL=diisobutylaluminum hydride
DMAP=4-(dimethylamino)-pyridine
DMF=N,N-dimethylformamide
DMSO=dimethylsulfoxide
ESIMS=electron spray mass spectrometry
$Et_3N$=triethylamine
EtOAc=ethyl acetate
HCl=hydrochloric acid
HMTA=hexamethylenetetramine
i.p.=intraperitoneal
LDA=lithium diisopropylamide
LHDMS=lithium bis(trimethylsily)amide
LiCl=lithium chloride
LPS=lipopolysaccharide
$MgSO_4$=magnesium sulfate
NaH=sodium hydride
$NH_4Cl$=ammonium chloride
NIS=N-iodosuccinimide NMP=1-methyl-2-pyrrolidinone
PBMC=peripheral blood mononuclear cell
$Pd_2(dba)_3$=tris(dibenzylideneacetone)dipalladium
PDC=pyridinium dichromate
Ph=phenyl
$Ph_2O$=diphenyl ether
p.o.=per os
Py=pyridinyl
PyBOP=benzotriazolyloyl-tris[pyrrolidino]-phosphonium hexafluorophosphate
r.t.=room temperature
s.c.=subcutaneous
TFA=trifluoroacetic acid
THF=tetrahydrofuran
TLC=thin layer chromatography
$Tf_2O$=trifluoromethanesulfonic anhydride
TMSCN=trimethylsilyl cyanide
$ZnI_2$=zinc iodide
The following alkyl group abbreviations are used.
Me=methyl
Et=ethyl
n-Pr=normal propyl
i-Pr=isopropyl
n-Bu=normal butyl
i-Bu=isobutyl
t-Bu=tertiary butyl
s-Bu=secondary butyl
c-Hex=cyclohexyl Biological Activity In Vitro Assay Enzyme-linked immunosorbent assays (ELISA) for TNFα can be performed in a conventional manner (*Blood*, 75, 40-47 (1990)). Human PBMC are isolated from heparinized venous blood obtained from healthy volunteers by Ficoll-Hypaque density centrifugation. The cells are cultured in RPMI1640 medium supplemented with 5% heat-inactivated fetal calf serum and antibiotics. PBMC (5×10E5 cells/mL) in 0.2 mL aliquot are pretreated with drugs in DMSO for 60 min at 37° C. in 96 well round-bottomed tissue culture plates. Thereafter, PBMC in the presence or absence of compound are stimulated with 1 mg/mL LPS from *E. coli* O55:B5 at a final concentration of 100 ng/mL. After overnight culture, the supernatants are harvested and assayed immediately for TNFα levels from each well. The concentration of TNFα in the supernatant is determined by human TNFα ELISA Kit according to the manufacture's directions.

Active compounds are characterized by the concentration of the compound that caused 50% inhibition of TNFα level ($IC_{50}$). The compounds with $IC_{50}$ less than or equal to 50 μM in this assay are considered to be active. The preferred compounds have the $IC_{50}$ value less than 10 μM. The most preferred compound have the $IC_{50}$ value less than 1 μM.

In Vivo Assay

Male C3H/HeN mice are administered p.o. or i.p. or s.c. with the compound just or 30 min or 60 min or 120 min before an i.p. challenge of 100 ng LPS. The serum concentration of TNFα for individual mouse is determined 90 min after the LPS challenge by a specific ELISA (Infection and Immunity, 64, 769-774 (1996)).

Compounds tested in this assay are considered to be active if the TNFα level is significantly decreased.

On the basis of these studies, and those known to the skilled artisan, it is readily apparent that the pharmacologically active compounds of this invention are useful for preparing pharmaceutical compositions for medical and veterinary use. Compound (1) and pharmaceutical compositions containing the same as an active ingredient have the effects of expected for TNFα reduction.

Table I summarises the in vitro biological activity (TNFα inhibition).

TABLE I

In Vitro Biological Activity

| Compounds | 50% Inhibition of TNFα level ($IC_{50}$, μM) |
|---|---|
| Example 1 | 0.36 |
| Example 2 | 0.09 |
| Example 3 | 0.58 |
| Example 4 | 2.1 |
| Example 5 | 19.3 |
| Example 6 | 12.9 |
| Example 7 | 1.17 |
| Example 8 | 18.7 |
| Example 9 | 0.85 |
| Example 10 | <0.6 |
| Example 11 | 0.13 |
| Example 12 | <0.6 |
| Example 13 | 0.68 |
| Example 15 | 9.4 |
| Example 16 | 6.8 |
| Example 17 | 50 |
| Example 18 | 23.6 |
| Example 19 | <0.6 |
| Example 21 | 10.5 |
| Example 23 | 10.3 |
| Example 24 | 10.4 |
| Example 25 | 13.7 |
| Compounds (Number of Examples) | |
| 14-1 | 0.36 |
| 14-2 | 0.32 |
| 14-4 | 0.44 |
| 14-5 | 3.7 |
| 14-6 | 1.6 |
| 14-7 | 1.0 |
| 14-8 | 0.14 |
| 14-9 | 4.6 |
| 14-10 | 0.58 |
| 14-12 | 0.06 |
| 14-14 | 0.40 |
| 14-15 | 0.06 |
| 14-16 | 9.6 |
| 14-17 | 0.12 |
| 14-18 | 3.9 |
| 14-19 | 0.85 |
| 14-20 | 0.49 |
| 14-21 | 3.0 |
| 14-23 | <0.6 |
| 14-24 | 0.46 |
| 14-25 | 0.31 |
| 14-26 | 0.05 |
| 14-27 | 0.06 |
| 14-30 | 6.47 |
| 14-31 | 2.20 |
| 14-32 | 1.3 |
| 14-33 | 8.40 |
| 14-35 | 0.45 |
| 14-36 | 0.13 |
| 14-43 | 6.6 |
| 14-44 | 7.5 |
| 14-45 | 3.2 |
| 14-46 | 5.6 |
| 14-52 | 11.6 |
| 14-56 | 4.5 |
| 14-60 | 1.1 |
| 14-61 | 5.8 |
| 14-64 | 2.1 |
| 14-65 | 2.7 |
| 14-66 | 5.2 |
| 14-67 | 1.7 |
| 14-69 | 2.4 |
| 14-71 | 2.4 |
| 14-72 | 1.9 |

TABLE I-continued

In Vitro Biological Activity

| | 50% Inhibition of TNFα level (IC$_{50}$, μM) |
|---|---|
| 14-73 | 1.7 |
| 14-74 | 0.24 |
| 14-77 | 0.9 |
| 14-78 | 1.3 |
| 14-79 | 1.6 |
| 14-80 | 2.4 |
| 14-81 | 0.34 |
| 14-82 | 1.17 |
| 14-83 | 0.78 |
| 14-84 | 1.67 |
| 14-104 | 2.1 |
| 14-105 | 0.09 |
| 20-1 | 9.4 |
| 20-2 | 6.8 |
| 20-4 | 9.5 |
| 20-5 | 8.8 |
| 20-10 | 10.4 |
| 20-13 | 7.5 |
| 20-14 | 9.7 |
| 20-19 | 7.2 |
| 20-20 | 6.6 |
| 20-21 | 2.8 |
| 20-22 | <0.6 |
| 20-26 | 9.8 |
| 20-27 | 5.1 |
| 20-28 | 1.2 |
| 20-29 | <0.6 |
| 20-30 | 5.8 |
| 20-31 | 9.8 |
| 20-32 | 11.4 |
| 20-34 | 10.6 |
| 20-37 | 11.8 |
| 20-39 | 5.4 |
| 20-40 | <0.6 |
| 20-41 | <0.6 |
| 20-42 | 2.2 |
| 20-43 | 3.1 |
| 20-44 | 0.3 |
| 20-45 | 7.2 |
| 20-46 | 0.96 |
| 20-47 | 0.31 |
| 20-48 | 1.8 |
| 20-49 | 10.9 |
| 20-50 | 4.5 |
| 20-54 | 6.7 |
| 20-55 | 6.4 |
| 20-56 | 7.8 |
| 20-57 | 3.6 |
| 20-58 | 11.9 |
| 20-59 | 5.9 |
| 20-60 | 4.4 |
| 20-61 | 0.65 |
| 20-64 | 11.7 |
| 22-1 | 9.1 |
| 22-2 | 6.6 |
| 22-3 | 10.1 |
| 22-4 | 6.0 |
| 22-5 | 1.8 |
| 22-6 | 0.25 |
| 22-7 | 4.2 |
| 22-8 | <0.6 |
| 22-9 | 0.27 |
| 22-10 | 2.5 |
| 22-11 | 3.2 |
| 26-1 | 6.30 |
| 26-6 | 10.3 |
| 26-11 | 9.0 |
| 26-15 | 11.8 |
| 26-16 | 8.6 |
| 26-22 | 8.2 |
| 26-24 | 1.7 |
| 26-28 | 10.4 |

Example 1

Preparation of dimethyl carbamic acid 2-oxo-2H-3-benzyl-4-methyl-1-benzopyran-7-yl ester

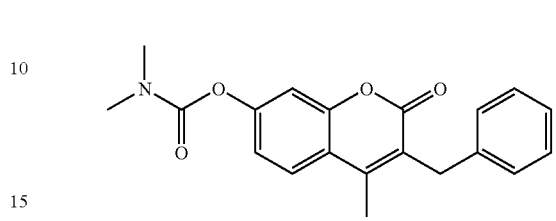

Step 1

Resorcinol (5.0 g) and ethyl 2-benzylacetoacetate (10.0 g) are mixed in 70% sulfuric acid (50 ml) at room temperature. The reaction mixture is stirred at room temperature overnight and poured into ice water. The solid is filtered and washed with water. The crude product is re-crystalized from EtOAc and hexane to afford 2-oxo-2H-3-benzyl-4-methyl-7-hydroxy-1-benzopyrane (10.6 g).

Step 2

To the solution of 2-oxo-2H-3-benzyl-4-methyl-7-hydroxy-1-benzopyrane (150 mg) DMF (4 ml) is added NaH (60%, 27 mg) at room temperature under nitrogen atmosphere. Dimethylcarbamoyl chloride (78 μl) is added to the reaction mixture after stirring for 15 minutes. The reaction mixture is stirred for 1 hour and poured into saturated NaHCO$_3$. The aqueous mixture is extracted three times with EtOAc. The combined organic extracts are washed with water three times and brine and dried over MgSO$_4$. Evaporation of the solvent gives the residue which is purified over preparative TLC (Hexane:EtOAc, 1:1) to afford the title compound, (169 mg) as colorless oil. $^1$HNMR δ2.44 (3H, s), 3.03 (3H, s), 3.12 (3H, s), 4.06 (2H, s), 7.07-7.26 (7H, m), 7.59 (1H, d); ESIMS: m/z 360 (M+Na).

Example 2

Preparation of dimethyl carbamic acid 2-oxo-2H-3-benzyl-4-methyl-6-chloro-1-benzopyran-7-yl ester

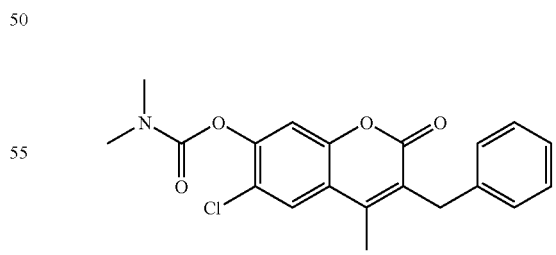

Step 1

4-Chlororesorcinol (26.25 g, 0.182 mol) and ethyl 2-benzylacetoacetate (40 g, 0.182 mol) are mixed in 70% H$_2$SO$_4$ (350 mL) at 0° C. The reaction mixture is stirred at room temperature for 72 hours and poured into ice water. The solid is filtered and washed with water. The crude product is recrystallized from ethanol/chloroform to afford 6-chloro-7-hydroxy coumarin intermediate (37.52 g, 68.7%).

Step 2

To the intermediate obtained above (300 mg, 1.0 mmol) in DMF (12, mL) is added NaH (60%, 50 mg) at room temperature under argon atmosphere. The reaction mixture is stirred for 30 min and dimethylcarbamoyl chloride (0.11 mL) is added. The reaction mixture is stirred at room temperature for 24 hours and poured into ice water. The aqueous mixture is extracted with diethyl ether three times. The combined organic extract is washed with brine and dried over $MgSO_4$. Evaporation of the solvent furnishes the crude solid which is re-crystallized from ethanol to afford the title compound (279 mg, 75.2%). $^1$HNMR δ2.40 (3H, s), 3.03 (3H, s), 3.15 (3H, s), 4.04 (2H, s), 7.19 (1H, m), 7.24 (5H, m), 7.63 (1H, s); ESIMS m/z 372 (M+H).

Example 3

Preparation of dimethyl carbamic acid 2-oxo-2H-3-benzyl-4-methyl-6-methoxy-1-benzopyran-7-yl ester

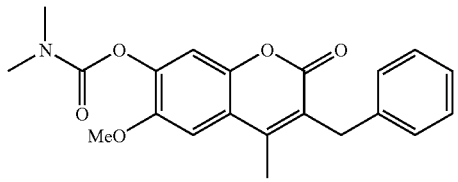

The title compound is prepared according to the above example. 4-methoxylresorcinol instead of 4-chlororesorcinol is used as starting material. $^1$H NMR δ2.40 (3H, s), 3.00 (3H, s), 3.12 (3H, s), 3.85 (3H, s), 4.05 (2H, s), 7.01 (1H, s), 7.10 (1H, s), 7.24 (5H, m); ESIMS m/z 368 (M+H).

Example 4

Preparation of dimethyl carbamic acid 2-oxo-2H-3-benzyl-4-(2-hydroxylethyl)1-benzopyran-7-yl ester

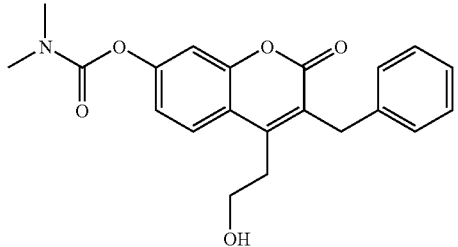

LHDMS (1.5 mL, 1.0 M in THF) is added to the solution of carbamic acid 2-oxo-3-benzyl-4-methyl-2H-1-benzopyran-7-yl ester (169 mg, cf. Example 1) in THF at −78° C. under argon atmosphere. The reaction was allowed to stir for 1 hour until the temperature is raised to 0° C. Paraformaldehyde (30 mg, 1 mmol) is added and the reaction is stirred for another 12 hour at room temperature. The reaction mixture is poured into ice water and extracted with EtOAc three times. The combined organic extract is washed with brine and dried over $MgSO_4$. Evaporation of the solvents gives the crude product that is purified over preparative TLC ($CH_2Cl_2$:acetone, 95:5) to afford the title compound (76 mg). $^1$HNMR δ2.98 (3H, s), 3.06 (2H, t), 3.10 (3H, s), 3.64 (2H, t), 4.02 (2H, s), 7.00 (1H, dd), 7.08 (1H, d), 7.20 (5H, m), 7.60 (1H, d); ESIMS m/z 368 (M+H).

Example 5

Preparation of dimethyl carbamic acid 2-oxo-2H-3-benzyl-4-(2-(2-pyridyl)$_2$-hydroxylethyl)-1-benzopyran-7-yl ester

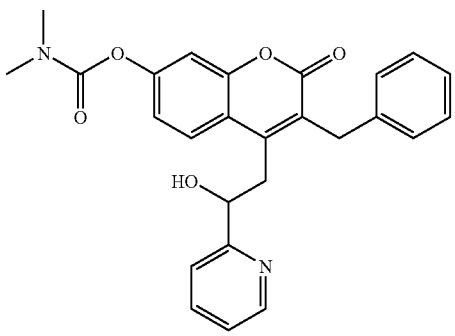

The title compound is prepared according to the above example. 2-Pyridinecarboxaldehyde instead of paraformaldehyde is used. $^1$H NMR δ2.98 (3H, s), 3.08 (3H, s), 3.28 (2H, m), 3.90 (2H, dd), 4.50 (1H, brs), 4.90 (1H, m), 6.98 (1H, dd), 7.02 (1H, d), 7.10-7.25 (7H, m), 7.62 (1H, ddd), 7.78 (1H, d), 8.50 (1H, dd); ESIMS m/z 445 (M+H).

Example 6

Preparation of dimethyl carbamic acid 2-oxo-2H-3-benzyl-4-methyl-8-formyl-1-benzopyran-7-yl ester

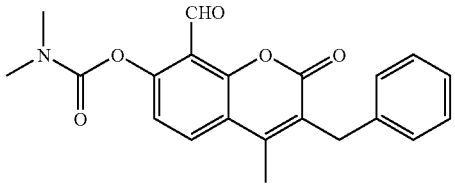

Step 1

2-Oxo-3-benzyl-4-methyl-7-hydroxyl-2H-1-benzopyrane (512 mg, Example 1) and HMTA (140 mg) are mixed in TFA (5 mL). The reaction mixture is heated at reflux overnight. The solvent is removed under reduced pressure. The residue is purified over silica gel column (Hexanes:EtOAc, 85:15) to afford the desired 8-formyl coumarin (107 mg) and 6-formyl coumarin derivative (35 mg).

Step 2

NaH (27 mg) is added to the solution of 8-formyl coumarin (97.5 mg) in DMF (1 mL) at room temperature under argon atmosphere. Dimethyl carbamoyl chloride (48 μL) is added to the solution after stirring for 10 minutes. The reaction mixture is stirred at room temperature for 4 hours and poured into ice water. The aqueous solution is extracted with EtOAc three times. The combined organic extract is washed with brine and dried over MgSO$_4$. Preparative TLC purification of the residue after evaporation of the solvent affords the title compound (34 mg). $^1$H NMR δ2.42 (3H, s), 3.02 (3H, s), 3.18 (3H, s), 4.05 (2H, s), 7.10 (1H, d), 7.15-7.30 (5H, m), 7.80 (1H, d), 10.68 (1H, s); ESIMS m/z 366 (M+H).

Example 7

Preparation of dimethyl carbamic acid 2-oxo-2H-3-(4-fluorobenzyl)4-n-propyl-1-benzopyran-7-yl ester

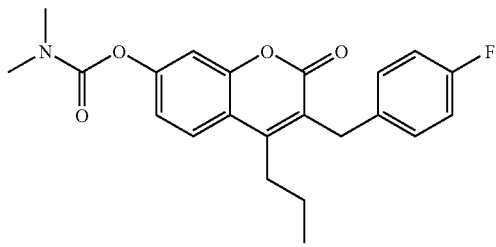

Step 1

NaH (480 mg, 60%) is added to the solution of ethyl butyrylacetate (1.58 mL, 10 mmol) in THF (30 mL) at 0° C. under argon atmosphere. The reaction mixture is stirred for 15 minutes and 4-fluorobenzyl bromide (1.37 mL, 11 mmol) is added. The reaction mixture is then heated to 60° C. for 2 hours. The reaction mixture is poured into ice cold saturated NH$_4$Cl and extracted with EtOAc three times. The combined organic extract is washed with brine and dried over MgSO$_4$. Concentration and column chromatography over silica gel (Hexanes:EtOAc, 75:25) of the residue give 2-(p-fluorophenylmethyl) butyrylacetate (1.21 g) as colorless oil.

Step 2

The ketoester obtained above (879 mg, 3.3 mmol) and resorcinol (330 mg, 3 mmol) are suspended in 5 mL of 70% sulfuric acid at room temperature. The reaction mixture is stirred for 2 hours and poured into ice water and extracted with EtOAc three times. The combined organic extract is washed with brine and dried over MgSO$_4$. Evaporation of the solvent affords 7-hydroxyl coumarin intermediate as colorless solid (217 mg).

Step 3

To the solution of coumarin intermediate obtained above (125 mg) in DMF (3 mL) is added NaH (19 mg) at room temperature under argon atmosphere. The reaction mixture is stirred for 15 minutes and dimethylcarbamoyl chloride (45 mL, 0.48 mmol) is added. The reaction mixture is stirred for another hour and poured into ice water. Extraction with EtOAc three times and the organic extract is combined. The combined organic extract is washed with brine and dried over MgSO$_4$. Purification of residue affords the title compound (162 mg). $^1$H NMR (CD$_3$OD) δ1.00 (3H, t), 1.48 (2H, m), 2.85 (2H, m), 3.00 (3H, s), 3.10 (3H, s), 4.01 (2H, s), 6.98 (2H, m), 7.14 (2H, m), 7.22 (2H, m), 7.78 (1H, d); ESIMS m/z 384 (M+H).

Example 8

Preparation of dimethyl carbamic acid 2-oxo-2H-3-benzyl-4-(m-pyridyl)-1-benzopyran-7-yl ester

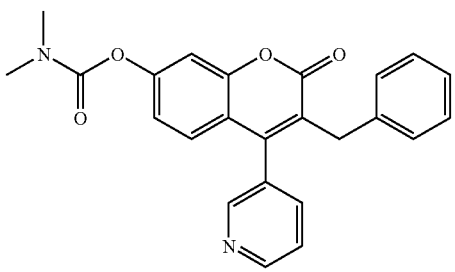

Step 1

NaH (300 mg; 60%) is added to the solution of methyl nicotinoylacetate (896 mg, 5 mmol) in THF (15 mL) at 0° C. under argon atmosphere. The reaction mixture is stirred for 15 minutes at the temperature and benzyl bromide (0.36 mL) is added. The reaction mixture is heated at reflux overnight. The reaction mixture is poured into iced 1N HCl and extracted with EtOAc three times. The combined organic extract is washed with brine and dried over MgSO$_4$. Concentration under reduced pressure gives the residue which is purified over column chromatography to afford methyl 2-benzyl-nicotinoylacetate intermediate (389 mg).

Step 2

The methyl 2-benzyl-nicotinoylacetate intermediate obtained above is mixed with resorcinol (159 mg) in 70% sulfuric acid. The reaction mixture is stirred at room temperature for 12 hours. Ice water is added to the reaction mixture which is then extracted with EtOAc three times. The combined organic extract is washed with brined and dried over MgSO$_4$. The residue (480 mg) obtained upon evaporation of the solvents is used directly in the next step.

Step 3

The coumarin intermediate obtained in step 2 (170 mg) is dissolved in DMF (5 mL). NaH (60%, 42 mg) is added to the solution at 0° C. under argon atmosphere. After stirring for 10 minutes, dimethylcarbamoyl chloride (72 μL) is added. The reaction mixture is stirred overnight at room temperature before it is poured into ice water. Extraction with EtOAc three times and the combined organic extract is washed with brine and dried over MgSO$_4$. Evaporation of the solvents give the residue which is purified over preparative TLC (CH$_2$Cl$_2$:MeOH, 95:5) to afford the title compound (40.5 mg). $^1$H NMR δ3.00 (3H, s), 3.10 (3H, s), 3.78 (2H, dd), 6.84 (1H, d), 6.92 (2H, m), 7.15 (4H, m), 7.40 (2H, m), 7.45 (1H, m), 8.42 (1H, brs), 8.78 (1H, brs); ESIMS m/z 401 (M+H).

Example 9

Preparation of dimethyl carbamic acid 2-oxo-2H-3-benzyl-4-methyl-6-cyano-1-benzopyran-7-yl ester

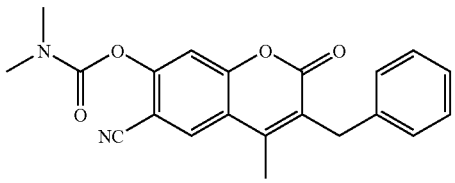

Step 1

2-Oxo-2H-3-benzyl-4-methyl-7-hydroxyl-1-benzopyrane (266 mg, 1 mmol, cf. Example 1) is dissolved in TFA (10 mL) at room temperature. NIS (248 mg, 1.1 mmol) is added and the reaction mixture is stirred for 12 hours. The solvent is removed under reduced pressure. The residue is dissolved in EtOAc and washed with water, brine and dried over $MgSO_4$. The crude product obtained after evaporation of the solvent is re-cryastallized from MeOH to afford the 6-iodo derivative (112 mg).

Step 2

NaH (48 mg, 60%) is added to the solution of 6-iodo coumarin obtained above (392 mg) in 5 mL of DMF under nitrogen atmosphere at room temperature. After stirring for 15 minutes, dimethylcarbamoyl chloride (0.11 mL, 1.2 mmol) is added and the reaction mixture is stirred for another 4 hours. The reaction mixture is poured into saturated $NH_4Cl$ and extracted with EtOAc three times. The combined organic extract is washed with brine and dried over $MgSO_4$. Concentration and purification with preparative TLC (Hexane:EtOAc, 4:1) afford 6-iodo carbamic acid ester intermediate (440 mg).

Step 3

The iodo carbamate intermediate obtained above (60 mg, 0.13 mmol) and CuCN (17 mg, 0.19 mmol) are mixed in DMF (5 mL). The mixture is heated at 130° C. under nitrogen atmosphere for 5 hours. The reaction mixture is poured into ice water and extracted with EtOAc three times. The combined organic extract is washed with brine and dried over $MgSO_4$. Concentration under reduced pressure and purification of the crude residue afford the title compound (23 mg). $^1H$ NMR $\delta 2.42$ (3H, s), 3.02 (3H, s), 3.20 (3H, s), 4.02 (2H, s), 7.20 (5H, m), 7.40 (1H, s), 7.82 (1H, s); ESIMS m/z 363 (M+H).

Example 10

Preparation of dimethyl carbamic acid 2-oxo-2H-3-benzyl-4-methyl-5-fluoro-1-benzopyran-7-yl ester

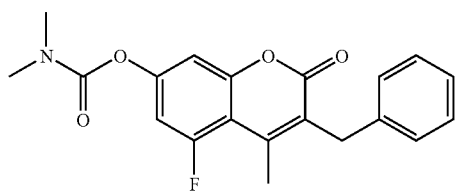

Step 1

1-Fluoro-3,5-dihydroxybenzene (1.0 g, 7.8 mmol) and ethyl 2-benzyl acetoacetate 1.72 g, 7.8 mmol) are suspended in 20 mL of 70% sulfuric acid at room temperature. The reaction mixture is stirred for 24 hours and poured into ice water. The solid is filtered and washed with water. The yellowish crude product is re-crystallized from hot ethanol to afford the 7-hydroxy coumarin intermediate (929 mg, 42%).

Step 2

To a suspension of NaH (60%, 45 mg, 1.05 mmol) in anhydrous THF (5 mL) is added the 7-hydroxy coumarin intermediate (200 mg, 0.7 mmol) at room temperature under argon atmosphere. The suspension is stirred for 30 min before adding dimethylcarbamoyl chloride (100 μL, 1.05 mmol). The reaction mixture is stirred overnight before pouring into aqueous ether. The ether is then washed twice with water, brine and dried over $MgSO_4$. Evaporation of the solvent gives a residue which is purified on a preparative TLC ($CHCl_3$: MeCN, 95:5) to afford the title compound (135 mg) as a colorless oil. $^1H$ NMR $\delta 2.53$ (3H, s), 3.01 (3H, s), 3.08 (3H, s), 4.03 (2H, s), 6.84 (1H, m), 6.93 (1H, s), 7.17 (1H, m), 7.23 (4H, m); ESIMS m/z 356 (M+H).

Example 11

Preparation of dimethyl carbamic acid 2-oxo-2H-3-(p-pyridinylmethyl)-4-methyl-6-chloro-1-benzopyran-7-yl ester

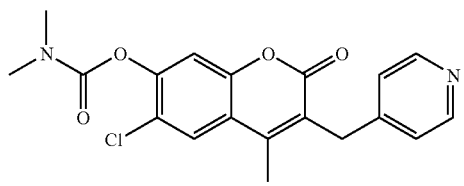

Step 1

Ethyl acetoacetate (5.20 g), pyridine-4-aldehyde (4.28 g), piperidine (0.4 ml) and AcOH (0.24 ml) are mixed in $CH_2Cl_2$ (150 ml) at room temperature under nitrogen atmosphere. The reaction mixture is stirred overnight and the solvent is removed. The residue is dissolved in EtOH (150 ml). 10% Pd/C (1.09) is added and reaction mixture is stirred at room temperature under hydrogen for 7 hours. Concentration under reduced pressure after Celite® filtration afford Ethyl 2-(4-piridylmethyl) acetoacetate (8.0 g) as colorless oil.

Step 2

The ketoester obtained above (4.59 g) and 4-chlororesorcinol (3.09) are suspended in 10 ml of 70% sulfuric acid at room temperature. The reaction mixture is stirred overnight and poured into water and is neutralized with NaOH aq. (Ph=7.0). The aqueous mixture is extracted three times with EtOAc. The combined organic extracts are dried over $MgSO_4$. The crude product obtained after evaporation of the solvent is re-crystallized from $CH_2Cl_2$ to afford the 2-oxo-2H-3-(4-pyridinylmethyl)$_4$-methyl-6-chloro-7-hydroxy-1-benzopyrane (291 mg).

Step 3

To the solution of 2-oxo-2H-3-(4-pyridinylmethyl)$_4$-methyl-6-chloro-7-hydroxy-1-benzopyrane (100 mg) DMF (3 ml) is added NaH (60%, 20 mg) at room temperature under nitrogen atmosphere. Dimethylcarbamoyl chloride (46 μl) is added to the reaction mixture after stirring for 15 minutes. The reaction mixture is stirred overnight and poured into saturated $NaHCO_3$. The aqueous mixture is extracted three times with EtOAc. The combined organic extracts are washed with water three times and brine and dried over $MgSO_4$. Evaporation of the solvent gives the residue which is purified over preparative TLC ($CHCl_3$:MeOH, 97:3) to afford the title compound (61 mg) as colorless oil. $^1H$ NMR $\delta 2.41$ (3H, s), 3.05 (3H, s), 3.18 (3H, s), 4.05 (2H, s), 7.16 (2H, d, J=5.9 Hz), 7.28 (1H, s), 7.67 (1H, s), 8.50 (2H, d, J=5.9 Hz); ESIMS m/z 395 (M+Na).

Example 12

Preparation of dimethyl carbamic acid 2-oxo-2H-3-(m-acetylamidobenzyl)-4-methyl-6-chloro-1-benzopyran-7-yl ester

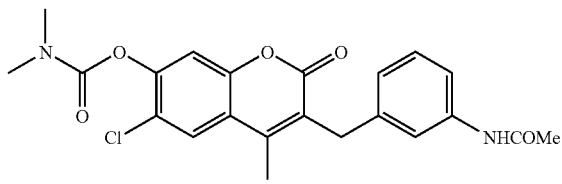

Step 1

NaH (1.94 g, 60%) is added to the solution of ethyl acetoacetate (6.029) in THF (100 ml) at 0° C. under nitrogen atmosphere. The reaction mixture is stirred for 15 minutes at the temperature and 3-nitrobenzylbromide (10 g) is added. The reaction mixture is stirred at room temperature overnight. The reaction mixture is poured into saturated $NH_4Cl$ aq. and extracted with EtOAc twice. The combined organic extract is washed with brine and dried over MgSO4. Concentration under reduced pressure gives the residue which is purified over column chromatography to afford ethyl 2-(3-nitrobenzyl)-acetoacetate (12 g).

Step 2

The ketoester intermediate (5.5 g) obtained above is mixed with 4-chlororesorcinol (3.0 g) in 70% sulfuric acid. The reaction mixture is stirred at room temperature for 3 days and poured into water. The solid is filtered and washed with water. The crude product is re-crystallized from acetone and hexane to afford 2-oxo-2H-3-(3-nitrobenzyl)-4-methyl-6-chloro-7-hydroxy-1-benzopyrane (3.20 g).

Step 3

To the solution 2-oxo-2H-3-(3-nitrobenzyl)-4-methyl-6-chloro-7-hydroxy-1-benzopyrane of (200 mg) DMF (5 ml) is added NaH (60%, 28 mg) at room temperature under nitrogen atmosphere. Dimethylcarbamoyl chloride (80 μl) is added to the reaction mixture after stirring for 15 minutes. The reaction mixture is stirred overnight and poured into saturated $NaHCO_3$. The aqueous mixture is extracted three times with EtOAc. The combined organic extracts are washed with water three times and brine and dried over $MgSO_4$. Evaporation of the solvent gives the residue which is re-crystallized from $CH_2Cl_2$ and hexane to afford dimethyl carbamic acid 2-oxo-2H-3-(3-nitrobenzyl)4-methyl-6-chloro-1-benzopyrane-7-yl ester (214 mg).

Step 4

To the solution of 2-oxo-2H-3-(3-nitrobenzyl)4-methyl-6-chloro-1-benzopyrane-7-yl ester (187 mg) DMF (5 ml) is added $SnCl_2 2H_2O$ (506 mg) at room temperature. The reaction mixture is stirred at room temperature for 4 hours and poured into saturated $NaHCO_3$ aq. The aqueous mixture is extracted three times with EtOAc. The combined organic extracts are washed with water three times and brine and dried over $MgSO_4$. Evaporation of the solvent gives the residue which is re-crystallized from $CH_2Cl_2$ and hexane to afford dimethyl carbamic acid 2-oxo-2H-3-(3-aminobenzyl)4-methyl-6-chloro-1-benzopyrane-7-yl ester (138 mg).

Step 5

To the solution of 2-oxo-2H-3-(3-aminobenzyl)4-methyl-6-chloro-J-benzopyrane-7-yl ester (106 mg) $CH_2Cl_2$ (3 ml) is added AcCl (39 μl) and $Et_3N$ (114 μl) at room temperature. The reaction mixture is stirred at room temperature for 1 hour and poured into saturated $NaHCO_3$ aq. The aqueous mixture is extracted three times with $CH_2Cl_2$. The combined organic extracts are dried over $MgSO_4$. Evaporation of the solvent gives the residue which is re-crystallized from $CH_2Cl_2$ and hexane to afford title compound (87 mg). $^1H$ NMR δ2.12 (3H, s), 2.42 (3H, s), 3.05 (3H, s), 3.17 (3H, s), 4.03 (2H, s), 6.99 (1H, d, J=7.6 Hz), 7.20-7.30 (4H, m), 7.43 (1H, d, J=7.6 Hz), 7.64 (1H, s); ESIMS m/z 451 (M+Na).

Example 13

Preparation of dimethyl thiocarbamic acid S-2-oxo-2H-3-benzyl-4-methyl-1-benzopyran-7-yl ester

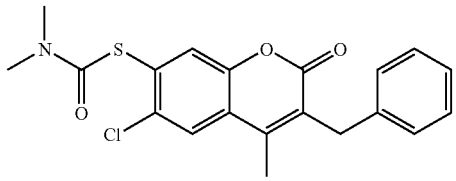

Step 1

NaH (90 mg, 60%, 2.25 mmol) is added to the solution of 2-oxo-2H-3-benzyl-4-methyl-7-hydroxyl-1-benzopyrane (500 mg, 1.88 mmol, Example 1) in DMF (5 mL) at 0° C. under argon atmosphere. After stirring for 10 minutes, dimethyl thiocarbamoyl chloride (280 mg, 2.25 mmol) is introduced into the reaction. The reaction mixture is stirred at room temperature for 2 hours and poured into ice water. The reaction mixture is extracted with EtOAc three times. Evaporation of the solvent gives the crude residue, which is re-crystallized from MeOH to afford the desired thiocarbamic acid O-ester intermediate (393 mg).

Step 2

The thiocarbamic acid O-ester (340 mg) obtained above is dissolved in diphenyl ether and the mixture is heated up to 220° C. for 4 hours. The reaction mixture is directly passed through a short silica gel column to afford the title compound (330 mg). $^1H$ NMR δ2.40 (3H, s), 3.00-3.10 (6H, brs), 4.02 (2H, s), 7.08-7.30 (5H, m), 7.40 (1H, d), 7.48 (1H, s), 7.60 (1H, d); ESIMS m/z 354 (M+H).

Example 14

The compounds in table II are prepared according to the indicated examples.

TABLE II

Compounds of formula (I) wherein R7 is dimethylcarbamoyloxyl group. In addition, for simplicity, $R_3$ is referred to as "Ar(methylene)" or "ArCH$_2$" in the structure and the table that follows, and thus only Ar is defined in the table.

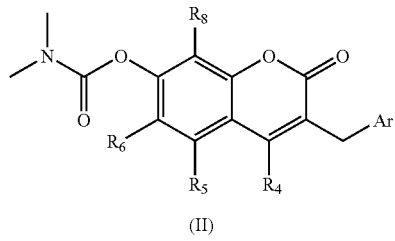

(II)

| Number of Examples | $R_4$ | $R_5, R_6, R_8$ | Ar | Physico-chemical Data (m/z, M + H or M + Na) | Process of Example |
|---|---|---|---|---|---|
| 14-1 | Me | $R_5 = R_6 = R_8 = H$ | Ph | 360 | 1 |
| 14-2 | Me | $R_5 = R_6 = R_8 = H$ | p-F—Ph | 378 | 1 |
| 14-3 | Me | $R_5 = Me_2NCO_2$, $R_6 = R_8 = H$ | Ph | 425 | 10 |
| 14-4 | Me | $R_5 = F$, $R_6 = R_8 = H$ | Ph | 356 | 10 |
| 14-5 | Me | $R_5 = F$, $R_6 = R_8 = H$ | m-NO$_2$Ph | 423 | 12 |
| 14-6 | Me | $R_5 = F$, $R_6 = R_8 = H$ | m-NH$_2$Ph | 393 | 12 |
| 14-7 | Me | $R_5 = F$, $R_6 = R_8 = H$ | m-MeCONHPh | 435 | 12 |
| 14-8 | Me | $R_5 = F$, $R_6 = R_8 = H$ | m-EtO$_2$CCH$_2$CONH—Ph | 484(M+) | 12 |
| 14-9 | Me | $R_6 = Et$, $R_5 = R_8 = H$ | Ph | 366 | 2 |
| 14-10 | Me | $R_6 = OMe$, $R_5 = R_8 = H$ | Ph | 368 | 2 |
| 14-11 | Me | $R_5 = OMe$, $R_6 = R_8 = H$ | Ph | 368 | 10 |
| 14-12 | Me | $R_6 = I$, $R_5 = R_8 = H$ | Ph | 464 | 9 |
| 14-13 | Me | $R_6 = iPr$, $R_5 = R_8 = H$ | Ph | 402 | 2 |
| 14-14 | Me | $R_6 = Me$, $R_5 = R_8 = H$ | Ph | 352 | 2 |
| 14-15 | Me | $R_6 = Br$, $R_5 = R_8 = H$ | Ph | 417 | 2 |
| 14-16 | Me | $R_6 = CHO$, $R_5 = R_8 = H$ | Ph | 366 | 6 |
| 14-17 | Me | $R_6 = NO_2$, $R_5 = R_8 = H$ | Ph | 383 | 6 |
| 14-18 | Me | $R_6 = TMSCC$, $R_5 = R_8 = H$ | Ph | 434 | 6 |
| 14-19 | Me | $R_6 = CN$, $R_5 = R_8 = H$ | Ph | 363 | 9 |
| 14-20 | Me | $R_6 = Cl$, $R_5 = R_8 = H$ | o-NH$_2$Ph | 409 | 12 |
| 14-21 | Me | $R_6 = Cl$, $R_5 = R_8 = H$ | o-NO$_2$Ph | 439 | 12 |
| 14-22 | Me | $R_6 = Cl$, $R_5 = R_8 = H$ | o-MeCONHPh | 451 | 12 |
| 14-23 | Me | $R_6 = Cl$, $R_5 = R_8 = H$ | m-NO$_2$Ph | 439 | 12 |
| 14-24 | Me | $R_6 = Cl$, $R_5 = R_8 = H$ | m-NH$_2$Ph | 409 | 12 |
| 14-25 | Me | $R_6 = Cl$, $R_5 = R_8 = H$ | m-MeCONHPh | 429 | 12 |
| 14-26 | Me | $R_6 = Cl$, $R_5 = R_8 = H$ | m-EtOCOCH$_2$CONH-Ph | 500(M+) | 12 |
| 14-27 | Me | $R_6 = Cl$, $R_5 = R_8 = H$ | (MeSO$_2$)$_2$NPh | 543(M+) | 12 |

TABLE II-continued

Compounds of formula (I) wherein R7 is dimethylcarbamoyloxyl group. In addition, for simplicity, $R_3$ is referred to as "Ar(methylene)" or "ArCH$_2$" in the structure and the table that follows, and thus only Ar is defined in the table.

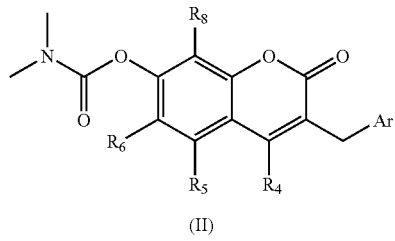

(II)

| Number of Examples | $R_4$ | $R_5, R_6, R_8$ | Ar | Physico-chemical Data (m/z, M + H or M + Na) | Process of Example |
|---|---|---|---|---|---|
| 14-28 | Me | $R_5 = R_6 = H$, $R_8 = Me$ | Ph | 374 | 2 |
| 14-29 | Me | $R_5 = R_6 = H$, $R_8 = CHO$ | Ph | 366 | 6 |
| 14-30 | Me | $R_5 = R_6 = R_8 = H$ | o-pyridinyl | 361 | 8 |
| 14-31 | Me | $R_5 = R_6 = R_8 = H$ | m-pyridinyl | 361 | 8 |
| 14-32 | Me | $R_5 = R_6 = R_8 = H$ | p-pyridinyl | 339 | 8 |
| 14-33 | Me | $R_5 = R_6 = H$, $R_8 = Me$ | m-pyridinyl | 375 | 8 |
| 14-34 | Me | $R_6 = Cl$, $R_5 = R_8 = H$ | o-pyridinyl | 373 | 8 |
| 14-35 | Me | $R_6 = Cl$, $R_5 = R_8 = H$ | m-pyridinyl | 395 | 8 |
| 14-36 | Me | $R_6 = Cl$, $R_5 = R_8 = H$ | p-pyridinyl | 395 | 8 |
| 14-37 | Me | $R_5 = R_6 = R_8 = H$ | 3',4',5'-trimethyloxylphenyl | 450 | 2 |
| 14-38 | Me | $R_5 = R_6 = R_8 = H$ | 3',4'-dichlorophenyl | | 2 |
| 14-39 | Me | $R_5 = R_6 = R_8 = H$ | 2',3',5'-trichlorophenyl | 441 | 2 |
| 14-40 | Me | $R_5 = R_6 = R_8 = H$ | 2',4',6'-trimethylphenyl | 380 | 2 |
| 14-41 | Me | $R_5 = R_6 = R_8 = H$ | Biphenyl | 414 | 2 |
| 14-42 | Me | $R_5 = H, R_6 = Et$ $R_8 = Me$ | Phenyl | 402 | 2 |
| 14-43 | Me | $R_5 = R_6 = R_8 = H$ | p-MeSO2Ph | 416 | 11 |
| 14-44 | Me | $R_5 = R_6 = R_8 = H$ | o-MeO—Ph | 368 | 11 |
| 14-45 | Me | $R_5 = R_6 = R_8 = H$ | m-MeO—Ph | 368 | 11 |
| 14-46 | Me | $R_5 = R_6 = R_8 = H$ | p-MeO—Ph | 368 | 11 |
| 14-47 | Me | $R_5 = R_6 = R_8 = H$ | p-Me$_2$N—Ph | 381 | 11 |
| 14-48 | Me | $R_5 = R_6 = R_8 = H$ | p-tBu—Ph | 394 | 11 |
| 14-49 | Me | $R_5 = R_6 = R_8 = H$ | o-CF$_3$—Ph | 406 | 11 |
| 14-50 | Me | $R_5 = R_6 = R_8 = H$ | m-CF$_3$—Ph | 406 | 11 |
| 14-51 | Me | $R_5 = R_6 = R_8 = H$ | p-CF$_3$—Ph | 406 | 11 |
| 14-52 | Me | $R_5 = R_6 = R_8 = H$ | p-i-Pr—Ph | 380 | 11 |
| 14-53 | Me | $R_5 = R_6 = R_8 = H$ | P-Et—Ph | 366 | 11 |
| 14-54 | Me | $R_5 = R_6 = R_8 = H$ | p-EtO—Ph | 382 | 11 |
| 14-55 | Me | $R_5 = R_6 = R_8 = H$ | o-NO$_2$—Ph | 383 | 11 |
| 14-56 | Me | $R_5 = R_6 = R_8 = H$ | m-NO$_2$—Ph | 383 | 11 |
| 14-57 | Me | $R_5 = R_6 = R_8 = H$ | p-NO$_2$—Ph | 383 | 11 |
| 14-58 | Me | $R_5 = R_6 = R_8 = H$ | p-MeO$_2$C—Ph | 396 | 11 |
| 14-59 | Me | $R_5 = R_6 = R_8 = H$ | o-MeCONHPh | 395 | 12 |
| 14-60 | Me | $R_5 = R_6 = R_8 = H$ | m-MeCONHPh | 395 | 12 |
| 14-61 | Me | $R_5 = R_6 = R_8 = H$ | p-MeCONHPh | 395 | 12 |
| 14-62 | Me | $R_5 = R_6 = R_8 = H$ | 2-Naphthyl | 388 | 11 |
| 14-63 | Me | $R_5 = R_6 = R_8 = H$ | p-HOOC—Ph | 382 | 11 |
| 14-64 | Me | $R_5 = R_6 = R_8 = H$ | o-NH$_2$—Ph | 353 | 12 |
| 14-65 | Me | $R_5 = R_6 = R_8 = H$ | m-NH$_2$—Ph | 353 | 12 |
| 14-66 | Me | $R_5 = R_6 = R_8 = H$ | p-NH$_2$—Ph | 353 | 12 |
| 14-67 | Me | $R_5 = R_6 = R_8 = H$ | m-MeO$_2$C—Ph | 396 | 12 |
| 14-68 | Me | $R_5 = R_6 = R_8 = H$ | m-HOOC—Ph | 382 | 12 |
| 14-69 | Me | $R_5 = R_6 = R_8 = H$ | m-EtNHCONH—Ph | 424 | 12 |

TABLE II-continued

Compounds of formula (I) wherein R7 is dimethylcarbamoyloxyl group. In addition, for simplicity, R₃ is referred to as "Ar(methylene)" or "ArCH₂" in the structure and the table that follows, and thus only Ar is defined in the table.

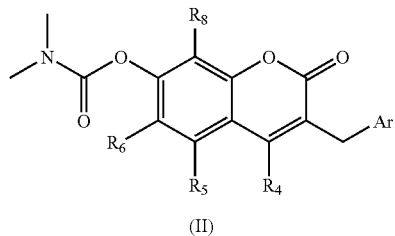

(II)

| Number of Examples | R₄ | R₅, R₆, R₈ | Ar | Physico-chemical Data (m/z, M + H or M + Na) | Process of Example |
|---|---|---|---|---|---|
| 14-70 | Me | R₅ = R₆ = R₈ = H | m-MeCONH—Ph | 395 | 12 |
| 14-71 | Me | R₅ = R₆ = R₈ = H | m-EtOCOCH₂NHCONH—Ph | 482 | 12 |
| 14-72 | Me | R₅ = R₆ = R₈ = H | m-Me₂N—Ph | 403 | 11 |
| 14-73 | Et | R₅ = R₆ = R₈ = H | Ph | 374 | 1 |
| 14-74 | Et | R₆ = Cl, R₅ = R₈ = H | Ph | 408 | 2 |
| 14-75 | Et | R₆ = Cl, R₅ = R₈ = H | m-NO₂Ph | 431 | 7 |
| 14-76 | Et | R₆ = Cl, R₅ = R₈ = H | m-NH₂Ph | 387 | 7 |
| 14-77 | Et | R₅ = R₆ = R₈ = H | m-NO₂Ph | 419 | 7 |
| 14-78 | Et | R₅ = R₆ = R₈ = H | m-NH₂Ph | 389 | 7 |
| 14-79 | Et | R₅ = R₆ = R₈ = H | m-CH₃CONHPh | 431 | 7 |
| 14-80 | Et | R₅ = R₆ = R₈ = H | p-pyridinyl | 375 | 7 |
| 14-81 | Et | R₆ = Cl, R₅ = R₈ = H | p-pyridinyl | 409 | 7 |
| 14-82 | n-Pr | R₅ = R₆ = R₈ = H | p-F—Ph | 384 | 7 |
| 14-83 | n-Pr | R₆ = Cl, R₅ = R₈ = H | Ph | 400 | 7 |
| 14-84 | Ph | R₅ = R₆ = R₈ = H | p-F—Ph | 418 | 7 |
| 14-85 | o-Pyridinyl | R₅ = R₆ = R₈ = H | Ph | 401 | 8 |
| 14-86 | PhCH₂CH₂ | R₅ = R₆ = R₈ = H | Ph | 428 | 5 |
| 14-87 | CH₂=CHC(Me)₂CH(OH)CH₂ | R₅ = R₆ = R₈ = H | | 450 | 5 |
| 14-88 | 2-Thiophene-CH(OH)CH₂ | R₅ = R₆ = R₈ = H | Ph | 450 | 5 |
| 14-89 | p-Me₂NPhCH(OH)CH₂ | R₅ = R₆ = R₈ = H | Ph | 487 | 5 |
| 14-90 | 5-Me-furanyl-CH(OH)CH₂ | R₅ = R₆ = R₈ = H | Ph | 448 | 5 |
| 14-91 | m-NO₂PHCH(OH)CH₂ | R₅ = R₆ = R₈ = H | Ph | 489 | 5 |
| 14-92 | MeSCH₂CH₂C1H(OH)CH₂ | R₅ = R₆ = R₈ = H | Ph | 442 | 5 |
| 14-93 | c-HexylCH(OH)CH₂ | R₅ = R₆ = R₈ = H | Ph | 450 | 5 |
| 14-94 | CH₂CHCH₂CH₂CH(OH)CH₂ | R₅ = R₆ = R₈ = H | Ph | 422 | 5 |
| 14-95 | p-CNPhCH(OH)CH₂ | R₅ = R₆ = R₈ = H | Ph | 469 | 5 |
| 14-96 | m-MePhCH(OH)CH₂ | R₅ = R₆ = R₈ = H | Ph | 458 | 5 |
| 14-97 | p-MeOPhCH(OH)CH₂ | R₅ = R₆ = R₈ = H | Ph | 474 | 5 |
| 14-98 | 2-FuranylCH(OH)CH₂ | R₅ = R₆ = R₈ = H | Ph | 434 | 5 |
| 14-99 | 2-Py-CH(OH)CH₂ | R₅ = R₆ = R₈ = H | Ph | 445 | 5 |
| 14-100 | 3-Py-CH(OH)CH₂ | R₅ = R₆ = R₈ = H | Ph | 445 | 5 |
| 14-101 | 2-thiazole-CH(OH)—CH₂ | R₅ = R₆ = R₈ = H | Ph | 451 | 5 |
| 14-102 | 4-Py-CH(OH)—CH₂ | R₅ = R₆ = R₈ = H | Ph | 445 | 5 |
| 14-103 | Ph-CH(OH)CH₂ | R₅ = R₆ = R₈ = H | Ph | 444 | 5 |
| 14-104 | HOCH₂CH₂ | R₅ = R₆ = R₈ = H | Ph | 368 | 4 |
| 14-105 | Me | R6 = Cl, R5 = R8 = H | Ph | 372 | 2 |

Example 15

Preparation of 2-oxo-2H-3-benzyl-4-methyl-7-(pyrimidin-2-yloxyl)-1-benzopyrane

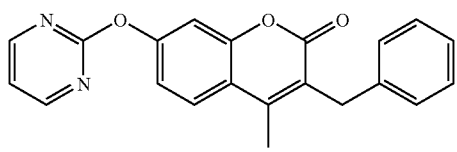

NaH (60%, 9 mg) is added to the solution of 2-oxo-2H-3-benzyl-4-methyl-7-hydroxyl-1-benzopyrane (50 mg) in DMF (2 ml) at room temperature under nitrogen atmosphere. After stirring for 15 minutes, 2-bromopyrimidine (36 mg) is added to the mixture. The reaction mixture is heated at 60° C. for 5 days. The reaction mixture is cooled down to room temperature and poured into saturated NaHCO$_3$ aq. The aqueous mixture is extracted with EtOAc twice. The combined organic extract is washed with water three times and brine and dried over MgSO$_4$. Evaporation of the solvent gives the residue which is purified over preparative TLC (Hexane:EtOAc, 1:1) to afford the title compound (54 mg) as colorless oil.

$^1$H NMR δ2.46 (3H, s), 4.08 (2H, s), 7.10-7.30 (8H, brs), 7.68 (1H, d, 8.9 Hz), 8.59 (2H, d, 4.95 Hz); ESIMS m/z 367 (M+Na).

Example 16

Preparation of 2-oxo-2H-3-benzyl-4-methyl-6-chloro-7-(pyrimidin-2-yloxyl-1-benzopyrane

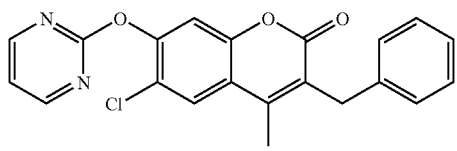

NaH (60%, 48 mg) is added to the solution of 2-oxo-2H-3-benzyl-4-methyl-6-chloro-7-hydroxyl-1-benzopyrane (300 mg) in DMF (10 ml) at room temperature under nitrogen atmosphere. After stirring for 15 minutes, 2-bromopyrimidine (190 mg) is added to the mixture. The reaction mixture is heated at 100° C. for 2 days.

The reaction mixture is cooled down to room temperature and poured into saturated NaHCO$_3$ aq. The aqueous mixture is extracted with EtOAc twice. The combined organic extract is washed with water three times and brine and dried over MgSO$_4$. Evaporation of the solvent gives the residue which is purified over preparative TLC (CHCl$_3$:MeOH, 99:1) to afford the title compound, (257 mg) as colorless oil. $^1$H NMR δ2.45 (3H, s), 4.08 (2H, s), 7.10-7.30 (7H, brs), 7.73 (1H, d), 8.59 (2H, d, J=4.6 Hz); ESIMS m/z 401 (M+Na).

Example 17

Preparation of 2-oxo-2H-3-(3-pyridylmethyl)-4-methyl-6-chloro-7-(pyrimidin-2-yloxyl)-1-benzopyrane

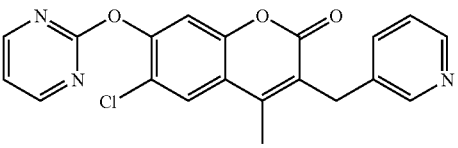

NaH (60%, 16 mg) is added to the solution of 2-oxo-2H-3-(3-pyridylmethyl)$_4$-methyl-6-chloro-7-hydroxyl-1-benzopyrane (100 mg) in DMF (3 ml) at room temperature under nitrogen atmosphere. After stirring for 15 minutes, 2-bromopyrimidine (63 mg) is added to the mixture. The reaction mixture is heated at 100° C. for 2 days. The reaction mixture is cooled down to room temperature and poured into saturated NaHCO$_3$ aq. The aqueous mixture is extracted with EtOAc twice. The combined organic extract is washed with water three times and brine and dried over MgSO$_4$. Evaporation of the solvent gives the residue which is purified over preparative TLC (100% EtOAc) to afford the title compound (28 mg) as colorless oil. $^1$H NMR δ2.49 (3H, s), 4.06 (2H, s), 7.13 (1H, t, J=4.6 Hz), 7.19-7.24 (1H, m), 7.30 (1H, s), 7.61 (1H, d, 7.9 Hz), 7.74 (1H, s), 8.46 (1H, m), 8.55 (1H, d, J=1.6 Hz), 8.58 (2H, d, J=4.6 Hz); ESIMS m/z 402 (M+Na).

Example 18

Preparation of 2-oxo-2H-3-benzyl-4-(2-hydroxylethyl)-6-chloro-7-(pyrimidin-2-yloxyl)-1-benzopyrane

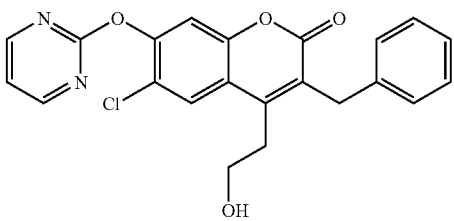

LHDMS (1.0M, 0.75 mL) is added to the solution of 2-oxo-2H-3-benzyl-4-methyl-6-chloro-7-(pyrimidin-2-yloxyl)-1-benzopyrane (189 mg, Example 16) in THF at −20° C. under argon atmosphere. The reaction mixture is stirred for 1 hour and paraformaldehyde (30 mg) is added. The reaction mixture is stirred at room temperature overnight and poured into saturated NH$_4$Cl. The mixture is extracted with EtOAc three times the combined organic extract is washed with 1H HCl, Sat. NaHCO$_3$ and brine and dried over MgSO$_4$. Evaporation of the solvent gives the crude residue which is purified over preparative TLC (CH$_2$Cl$_2$:Acetone, 95:5) to afford the title compound (49 mg). $^1$H NMR δ3.15 (2H, t), 3.80 (2H, t), 4.10 (2H, s), 7.09 (1H, m), 7.15-7.25 (7H, m), 7.79 (1H, s), 8.48 (2H, d); ESIMS m/z 409 (M+H).

Example 19

Preparation of 2-oxo-2H-3-(m-ethoxycarbonyl-acetylaminobenzyl)-4-methyl-7-(pyrimidin-2-yloxyl)-1-benzopyrane

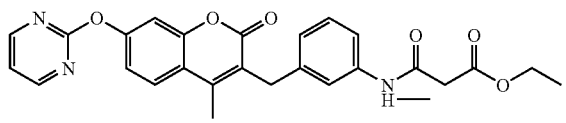

Step 1

Ethyl 2-(3-nitrobenzyl)-acetoacetate (2.65 g) obtained above is mixed with resorcinol (1.1 g) in 70% sulfuric acid. The reaction mixture is stirred at room temperature for 3 days and poured into water. The aqueous mixture is extracted three times with EtOAc and dried over $MgSO_4$. Evaporation of the solvent affords 2-oxo-2H-3-(3-nitrobenzyl)$_4$-methyl-7-hydroxy-1-benzopyrane (2.20 g).

Step 2

To the solution 2-oxo-2H-3-(3-nitrobenzyl)-4-methyl-7-hydroxy-1-benzopyrane of (400 mg) DMF (10 ml) is added NaH (60%, 62 mg) at room temperature under nitrogen atmosphere. 2-bromopyrimidine (306 mg) is added to the reaction mixture after stirring for 15 minutes. The reaction mixture is stirred at 90° C. for 2 hours and poured into saturated $NaHCO_3$. The aqueous mixture is extracted three times with EtOAc. The combined organic extracts are washed with water three times and brine and dried over $MgSO_4$. Evaporation of the solvent gives the residue which is re-crystallized from $Et_2O$ to afford 2-oxo-2H-3-(3-nitrobenzyl)$_4$-methyl-7-(pyrimidine-2-yloxyl)-1-benzopyrane (404 mg).

Step 3

To the solution of 2-oxo-2H-3-(3-nitrobenzyl)$_4$-methyl-7-(pyrmidine-2-yloxyl)-1-benzopyrane (270 mg) in EtOAc (10 ml) and AcOH (2 ml) is added 10% Pd/C (30 mg) at room temperature. The reaction mixture is stirred at room temperature overnight under hydrogen and filtered through Celite®. Evaporation of the solvent gives the residue which is re-crystallized from $CH_2Cl_2$ and hexane to afford 2-oxo-2H-3-(3-aminobenzyl)$_4$-methyl-7-(pyrimidine-2-yloxyl)-1-benzopyrane (190 mg).

Step 4

To the solution of 2-oxo-2H-3-(3-aminobenzyl)$_4$-methyl-7-(pyrimidine-2-yloxyl)-1-benzopyrane (70 mg) $CH_2Cl_2$ (3 ml) is added ethylmalonylchloride (37 µl) and $Et_3N$ (81 µl) at room temperature. The reaction mixture is stirred at room temperature for overnight and poured into saturated $NaHCO_3$ aq. The aqueous mixture is extracted three times with $CH_2Cl_2$. The combined organic extracts are dried over $MgSO_4$. Evaporation of the solvent gives the residue which is purified over preparative TLC (100% EtOAc) to afford the title compound (76 mg) as colorless oil. $^1H$ NMR δ1.31 (3H, t, J=7.25 Hz), 2.48 (3H, s), 3.44 (2H, s), 4.06 (2H, s), 4.25 (1H, q, J=7.25 Hz), 7.00-7.30 (5H, m), 7.43, 1H, d, J=7.6 Hz), 7.40-7.50 (2H, m), 7.68 (1H, d, J=4.6 Hz), 8.59 (1H, J=4.6 Hz), 9.10 (1H, brs); ESIMS m/z 496 (M+Na).

Example 20

The compounds in table III are prepared according to the indicated examples.

TABLE III

Compounds of formula (I) wherein $R_7$ is pyrimidin-2-yloxyl group. In addition, for simplicity, $R_3$ is referred to as "Ar(methylene)" or "ArCH$_2$" in the structure and the table that follows, and thus only Ar is defined in the table.

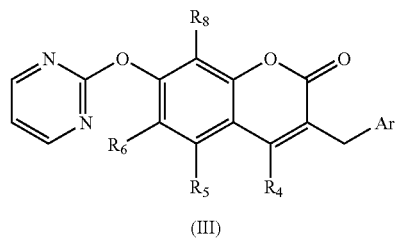

(III)

| Number of Examples | $R_4$ | $R_5$, $R_6$, $R_8$ | Ar | Physico-chemical Data (m/z, M + H or M + Na) | Process of Example |
|---|---|---|---|---|---|
| 20-1 | Me | $R_5 = R_6 = R_8 = H$ | Ph | 367 | 15 |
| 20-2 | Me | $R_6 = Cl, R_5 = R_8 = H$ | Ph | 401 | 16 |
| 20-3 | Me | $R_6 = iPr, R_5 = R_8 = H$ | Ph | 409 | 16 |
| 20-4 | Me | $R_6 = Br, R_5 = R_8 = H$ | Ph | 424 | 16 |
| 20-5 | Me | $R_6 = I, R_5 = R_8 = H$ | Ph | 471 | 16 |
| 20-6 | Me | $R_6 = Me, R_5 = R_8 = H$ | Ph | 359 | 16 |
| 20-7 | Me | $R_6 = Et, R_5 = R_8 = H$ | Ph | 373 | 16 |
| 20-8 | Me | $R_6 = OMe, R_5 = R_8 = H$ | Ph | 375 | 16 |
| 20-8 | Me | $R_5 = R_6 = R_8 = H$ | o-Pyridinyl | 346 | 17 |
| 20-9 | Me | $R_5 = R_6 = R_8 = H$ | m-Pyridinyl | 346 | 17 |
| 20-10 | Me | $R_5 = R_6 = R_8 = H$ | p-Pyridinyl | 368 | 17 |

TABLE III-continued

Compounds of formula (I) wherein $R_7$ is pyrimidin-2-yloxyl group. In addition, for simplicity, $R_3$ is referred to as "Ar(methylene)" or "ArCH$_2$" in the structure and the table that follows, and thus only Ar is defined in the table.

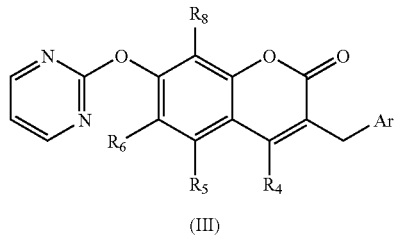

(III)

| Number of Examples | $R_4$ | $R_5, R_6, R_8$ | Ar | Physico-chemical Data (m/z, M + H or M + Na) | Process of Example |
|---|---|---|---|---|---|
| 20-11 | Me | $R_6$ = Cl, $R_5$ = $R_8$ = H | o-Pyridinyl | 381 | 17 |
| 20-12 | Me | $R_6$ = Cl, $R_5$ = $R_8$ = H | m-Pyridinyl | 402 | 17 |
| 20-13 | Me | $R_6$ = Cl, $R_5$ = $R_8$ = H | p-Pyridinyl | 402 | 17 |
| 20-14 | Me | $R_5$ = F, $R_6$ = $R_8$ = H | Ph | 363 | 16 |
| 20-15 | Me | $R_5$ = $R_6$ = $R_8$ = H | m-MeO$_2$C—Ph | 403 | 19 |
| 20-16 | Me | $R_5$ = $R_6$ = $R_8$ = H | m-HO$_2$C—Ph | 399 | 19 |
| 20-17 | Me | $R_5$ = $R_6$ = $R_8$ = H | m-Me$_2$N—Ph | 410 | 19 |
| 20-18 | Me | $R_5$ = $R_6$ = $R_8$ = H | m-NO$_2$—Ph | 412 | 19 |
| 20-19 | Me | $R_5$ = $R_6$ = $R_8$ = H | m-NH$_2$—Ph | 382 | 19 |
| 20-20 | Me | $R_5$ = $R_6$ = $R_8$ = H | m-MeCONH—Ph | 424 | 19 |
| 20-21 | Me | $R_5$ = $R_6$ = $R_8$ = H | m-EtOCOCH$_2$CH$_2$CONH—Ph | 510 | 19 |
| 20-22 | Me | $R_5$ = $R_6$ = $R_8$ = H | m-EtOCOCH$_2$CH$_2$CONH—Ph | 496 | 19 |
| 20-23 | Me | $R_5$ = $R_6$ = $R_8$ = H | m-HOOCCH$_2$CH$_2$CONH—Ph | 482 | 19 |
| 20-24 | Me | $R_5$ = $R_6$ = $R_8$ = H | m-HOOCCH$_2$CH$_2$CONH—Ph | 468 | 19 |
| 20-25 | Me | $R_6$ = Cl, $R_5$ = $R_8$ = H | m-NO$_2$—Ph | 424 | 19 |
| 20-26 | Me | $R_6$ = Cl, $R_5$ = $R_8$ = H | m-NH$_2$—Ph | 394 | 19 |
| 20-27 | Me | $R_6$ = Cl, $R_5$ = $R_8$ = H | m-Me$_2$N—Ph | 444 | 19 |
| 20-28 | Me | $R_5$ = Cl, $R_6$ = $R_8$ = H | m-EtOCOCH$_2$CH$_2$CONH—Ph | 544 | 19 |
| 20-29 | Me | $R_6$ = Cl, $R_5$ = $R_8$ = H | m-EtOCOCH$_2$CH$_2$CONH—Ph | 530 | 19 |
| 20-30 | Me | $R_6$ = Cl, $R_5$ = $R_8$ = H | MeCONHCH$_2$CONH—Ph | 515 | 19 |
| 20-31 | Me | $R_6$ = Cl, $R_5$ = $R_8$ = H | m-BnOCONHCH$_2$CONH—Ph | 607 | 19 |
| 20-32 | Me | $R_6$ = Cl, $R_5$ = $R_8$ = H | m-BnOCONHCH$_2$CONH—Ph | 621 | 19 |
| 20-33 | Me | $R_6$ = Cl, $R_5$ = $R_8$ = H | m-HOOCCH$_2$CH$_2$CONH—Ph | 516 | 19 |
| 20-34 | Me | $R_6$ = Cl, $R_5$ = $R_8$ = H | m-HOOCCH$_2$CH$_2$CONH—Ph | 502 | 19 |
| 20-35 | Me | $R_5$ = Cl, $R_6$ = $R_8$ = H | m-NO$_2$—Ph | 446 | 19 |
| 20-36 | Me | $R_5$ = Cl, $R_6$ = $R_8$ = H | m-NH$_2$—Ph | 416 | 19 |
| 20-37 | Me | $R_5$ = Cl, $R_6$ = $R_8$ = H | m-MeCONH—Ph | 458 | 19 |
| 20-38 | Me | $R_5$ = F, $R_6$ = $R_8$ = H | m-NO$_2$—Ph | 430 | 19 |
| 20-39 | Me | $R_5$ = F, $R_6$ = $R_8$ = H | m-MeCONH—Ph | 442 | 19 |
| 20-40 | Me | $R_5$ = F, $R_6$ = $R_8$ = H | m-EtOCOCH$_2$CONH—Ph | 514 | 19 |
| 20-41 | Me | $R_6$ = Cl, $R_5$ = $R_8$ = H | m-MeSO$_2$NH—Ph | 494 | 19 |
| 20-42 | Me | $R_6$ = Cl, $R_5$ = $R_8$ = H | m-MeCOCH$_2$CONH—Ph | 477(M−) | 10 |
| 20-43 | Me | $R_6$ = Cl, $R_5$ = $R_8$ = H | m-MeCONH—Ph | 436 | 19 |
| 20-44 | Me | $R_6$ = Cl, $R_5$ = $R_8$ = H | m-EtSO$_2$NH—Ph | 485(M−) | 19 |
| 20-45 | Me | $R_6$ = Cl, $R_5$ = $R_8$ = H | m-(p-tolyl-SO$_2$NH)—Ph | 547(M−) | 19 |
| 20-46 | Me | $R_6$ = Cl, $R_5$ = $R_8$ = H | m-nPrSO$_2$NH—Ph | 499(M−) | 19 |
| 20-47 | Me | $R_6$ = Cl, $R_5$ = $R_8$ = H | m-iPrSO$_2$NH—Ph | 499(M−) | 19 |
| 20-48 | Me | $R_6$ = Cl, $R_5$ = $R_8$ = H | m-nBuSO$_2$NH—Ph | 514(M−) | 19 |
| 20-49 | Et | $R_5$ = $R_6$ = $R_8$ = H | Ph | 381 | 15 |
| 20-50 | Et | $R_6$ = Cl, $R_5$ = $R_8$ = H | Ph | 415 | 16 |
| 20-51 | Et | $R_5$ = $R_6$ = $R_8$ = H | p-Pyridinyl | 382 | 17 |
| 20-52 | Et | $R_5$ = $R_6$ = $R_8$ = H | m-NO$_2$—Ph | 426 | 19 |
| 20-53 | Et | $R_5$ = $R_6$ = $R_8$ = H | m-NH$_2$—Ph | 396 | 19 |
| 20-54 | Et | $R_5$ = $R_6$ = $R_8$ = H | m-MeCONH—Ph | 438 | 19 |
| 20-55 | Et | $R_6$ = Cl, $R_5$ = $R_8$ = H | m-NO$_2$—Ph | 460 | 19 |
| 20-56 | Et | $R_6$ = Cl, $R_5$ = $R_8$ = H | m-NH$_2$—Ph | 430 | 19 |
| 20-57 | Et | $R_6$ = Cl, $R_5$ = $R_8$ = H | m-MeCONH—Ph | 472 | 19 |
| 20-58 | Et | $R_5$ = F, $R_6$ = $R_8$ = H | m-NO$_2$—Ph | 444 | 19 |
| 20-59 | Et | $R_5$ = F, $R_6$ = $R_8$ = H | m-NH$_2$—Ph | 414 | 19 |
| 20-60 | Et | $R_5$ = F, $R_6$ = $R_8$ = H | m-MeCONH—Ph | 456 | 19 |
| 20-61 | Et | $R_5$ = F, $R_6$ = $R_8$ = H | m-EtOCOCH$_2$CONH—Ph | 528 | 19 |
| 20-62 | n-Pr | $R_5$ = $R_6$ = $R_8$ = H | Ph | 395 | 19 |
| 20-63 | HOOCCH$_2$ | $R_5$ = $R_6$ = $R_8$ = H | Ph | 423 | 18 |

TABLE III-continued

Compounds of formula (I) wherein $R_7$ is pyrimidin-2-yloxyl group. In addition, for simplicity, $R_3$ is referred to as "Ar(methylene)" or "ArCH$_2$" in the structure and the table that follows, and thus only Ar is defined in the table.

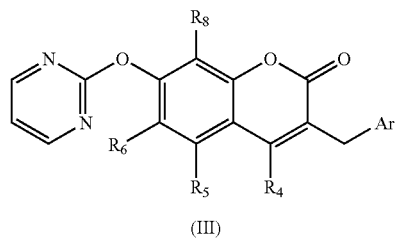

(III)

| Number of Examples | $R_4$ | $R_5, R_6, R_8$ | Ar | Physico-chemical Data (m/z, M + H or M + Na) | Process of Example |
|---|---|---|---|---|---|
| 20-64 | HOCH$_2$CH$_2$ | $R_6$ = Cl, $R_5$ = $R_8$ = H | Ph | 409 | 18 |
| 20-65 | Ph | $R_5$ = $R_6$ = $R_8$ = H | Ph | 429 | 15 |
| 20-66 | Ph | $R_5$ = $R_6$ = $R_8$ = H | o-Pyridinyl | 408 | 15 |
| 20-67 | Ph | $R_5$ = $R_6$ = $R_8$ = H | m-Pyridinyl | 408 | 15 |
| 20-68 | Ph | $R_5$ = $R_6$ = $R_8$ = H | p-Pyridinyl | 430 | 15 |
| 20-69 | m-Pyridinyl | $R_6$ = Cl, $R_5$ = $R_8$ = H | Ph | 442 | 16 |
| 20-70 | o-Pyridinyl | $R_6$ = Cl, $R_5$ = $R_8$ = H | Ph | 442 | 16 |
| 20-71 | p-Pyridinyl | $R_6$ = Cl, $R_5$ = $R_8$ = H | Ph | 442 | 16 |
| 20-72 | Me | $R_6$ = Cl, $R_5$ = $R_8$ = H | PhCH$_2$OCH$_2$CONHPh | 542 | 16 |

Example 21

Preparation of 2-oxo-3-benzyl-4-methyl-7-(thiazol-2-yloxyl)-2H-1-benzopyrane

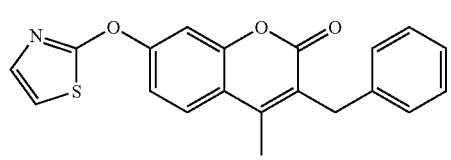

NaH (60%, 18 mg) is added to the solution of 2-oxo-2H-3-benzyl-4-methyl-7-hydroxyl-1-benzopyrane (100 mg) in DMF (3 ml) at room temperature under nitrogen atmosphere. After stirring for 15 minutes, 2-bromothiazole (40 μl) is added to the mixture. The reaction mixture is heated at 100° C. for 2 days. The reaction mixture is cooled down to room temperature and poured into saturated NaHCO$_3$ aq. The aqueous mixture is extracted with EtOAc twice. The combined organic extract is washed with water three times and brine and dried over MgSO$_4$. Evaporation of the solvent gives the residue which is purified over preparative TLC (Hexane:EtOAc, 1:1) to afford the title compound (22 mg) as colorless oil. $^1$H NMR δ2.45 (3H, s), 4.07 (2H, s), 6.91 (1H, d), 7.15-732 (8H, m), 7.65 (1, m d); ESIMS m/z 372 (M+Na).

Example 22

The compounds in table IV are prepared in accordance with Example 21.

TABLE IV

Compounds of formula (I) wherein R7 is thiazol-2-yloxyl group. In addition, for simplicity, $R_3$ is referred to as "Ar(methylene)" or "ArCH$_2$"in the structure and the table that follows, and thus only Ar is defined in the table.

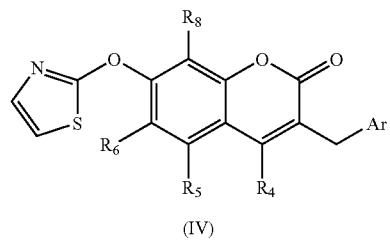

(IV)

| Number of Examples | $R_4$ | $R_5, R_6, R_8$ | Ar | Physico-chemical Data (m/z, M + H or M + Na) |
|---|---|---|---|---|
| 22-1 | Me | $R_5$ = $R_6$ = $R_8$ = H | Ph | 372 |
| 22-2 | Me | $R_5$ = $R_6$ = $R_8$ = H | m-NO$_2$PH | 417 |
| 22-3 | Me | $R_5$ = F, $R_6$ = $R_8$ = H | m-NO$_2$Ph | 435 |
| 22-4 | Me | $R_5$ = $R_6$ = $R_8$ = H | m-NH$_2$—Ph | 387 |
| 22-5 | Me | $R_5$ = $R_6$ = $R_8$ = H | m-MeCONH—Ph | 427 |
| 22-6 | Me | $R_5$ = $R_6$ = $R_8$ = H | m-EtOCOCH$_2$CONH—Ph | 501 |
| 22-7 | Et | $R_5$ = $R_6$ = $R_8$ = H | m-NH$_2$—Ph | 401 |
| 22-8 | Et | $R_5$ = $R_6$ = $R_8$ = H | m-MeCONH—Ph | 443 |
| 22-9 | Et | $R_5$ = $R_6$ = $R_8$ = H | EtOCOCH$_2$CONH—Ph | 515 |
| 22-10 | Et | $R_5$ = $R_6$ = $R_8$ = H | Ph | 386 |
| 22-11 | Et | $R_5$ = $R_6$ = $R_8$ = H | m-NO$_2$—Ph | 431 |
| 22-12 | Et | $R_5$ = $R_6$ = $R_8$ = H | m-EtO$_2$SNHPh | 471 |
| 22-13 | Et | $R_5$ = $R_6$ = $R_8$ = H | m-PhCH$_2$OCH$_2$OCNHPh | 527 |

Example 23

Preparation of 2-oxo-3-benzyl-4-methyl-7-vinyl-2H-1-benzopyrane

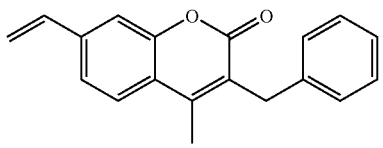

Step 1

Triflic anhydride (0.38 mL) is dropwise added to the solution of 2-oxo-2H-3-benzyl-4-methyl-7-hydroxyl-1-benzopyrane (284 mg) in 2,6-lutidine (3 mL) at room temperature under argon atmosphere. The reaction mixture is stirred at room temperature for 12 hours and poured into ice water. The aqueous mixture is extracted with EtOAc three times and the combined organic extract is washed with 1N HCl, brine and dried over MgSO$_4$. Purification of the crude residue with silica gel column (Hexane:EtOAc, 4:1) affords the triflate intermediate in quantitative yield (430 mg).

Step 2

The triflate intermediate obtained above (50 mg, 0.12 mmol) is mixed with LiCl (15 mg), trifurylphosphine (2 mg) and Pd$_2$(dba)$_3$ (2 mg) in 2 mL of NMP at room temperature under argon atmosphere. Tributyl vinyltin is added dropwise to the solution and the reaction mixture is stirred overnight. Potassium fluoride is added and the mixture is extracted with EtOAc three time and dried over MgSO$_4$. Concentration and purification of the residue with preparative TLC (Hexane:EtOAc, 3:1) afford the title compound (26 mg). $^1$H NMR δ2.40 (3H, s), 4.02 (2H, s), 5.40 (1H, d), 5.82 (1H, d), 6.70 (1H, dd), 7.15-7.30 (7H, m), 7.58 (1H, m); ESIMS m/z 277 (M+H).

Example 24

Preparation of 2-oxo-3-benzyl-4-methyl-7-(N,N-dimethylaminocarboxy-difluoromethyl)-1H-benzopyrane

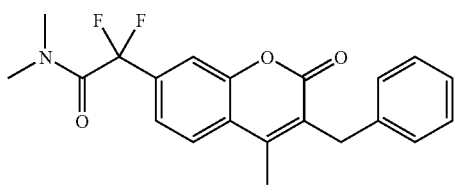

Step 1

To the suspension of 2-oxo-3-benzyl-4-methyl-7-vinyl-2H-1-benzopyrane (16.0 g, Example 23) in dioxane (350 mL) and water (75 mL) is added osmium tetraoxide (1.45 mmol) in t-BuOH. The reaction mixture is stirred at room temperature for 30 minutes and sodium periodate (30 g) is added in portions. The solid is filtered out after 30 minutes stirring and the filtrate is partitioned between CH$_2$Cl$_2$ and water. Separation and the organic layer is washed further with H$_2$O and dried over MgSO$_4$. Evaporation of the organic solvent gives the desired 7-formyl coumarin intermediate (12.0 g).

Step 2

To the mixture of the above intermediate (1.5 g) and ZnI$_2$ (172 mg) in CH$_2$Cl$_2$ (40 mL) is added TMSCN (1.44 mL) at room temperature. The reaction mixture is stirred for 16 hours and quenched with 2% HCl (50 mL). The mixture is extracted with CH$_2$Cl$_2$ and passed through a pad of Celite®. The organic extract is washed with 1N HCl, brine and dried over MgSO$_4$. Evaporation of the organic solvent gives the residue which is treated with 2.5 mL of TFA for 30 minutes. Evaporation of the solvent and purification of the crude product with silica gel column (EtOAc:Hexanes; 1:1) afford the desired cyanohydrin intermediate (1.34 g, 82%).

Step 3

The cyanohydrin (1.2 g) intermediate obtained above is dissolved in acetic acid (50 mL) and concentrated HCl (50 mL) and stirred for 68 hours at room temperature. The reaction mixture is extracted with EtOAc three times. The organic extract is washed with 1N HCl, brine and dried over MgSO$_4$. Evaporation of the solvent gives the crude α-hydroxyacid (1.059) which is used directly without further purification.

Step 4

To the solution of α-hydroxyacid (400 mg) obtained above in THF (10 mL) is added Me$_2$N, Et$_3$N (0.34 mL) followed by PyBOP (1.28 g) at room temperature. The reaction mixture is stirred for 2 hours and solvents are evaporated. The residue is diluted with EtOAc and washed with 1N HCl, saturated NaHCO$_3$, brine and dried over MgSO$_4$. The residue is purified with preparative TLC (CH$_2$Cl$_2$:MeOH:AcOH, 10:1:0.5) to afford the α-hydroxyamide (233 mg, 54%).

Step 5

PDC (106 mg) is added to the solution of α-hydroxyamide (66 mg) in CH$_2$Cl$_2$ (2 mL) at room temperature. The reaction mixture is stirred for 16 hours and filtered through a pad of Celite®. The filtrate is concentrated and purified over preparative TLC (CH$_2$Cl$_2$:MeOH, 20:1) to afford the ketoamide derivative (42 mg, 64%).

Step 6

DAST is added to the ketoamide intermediate (21 mg) in CH$_2$Cl$_2$ at room temperature. The reaction mixture is stirred for 16 hours. Dichloromethane is removed and another portion of DAST is added and the reaction mixture is heated at 60° C. for 24 hours. The reaction mixture is diluted with EtOAc and washed with brine and dried over MgSO$_4$. Purification of the residue after removal of the organic solvent affords the title compound (12.0 mg, 63%). $^1$HNMR δ2.42 (3H, s), 3.04 (3H, s), 3.10 (3H, s), 4.08 (2H, s), 7.18 (1H, m), 7.20-7.30 (3H, m), 7.42 (2H, d), 7.50 (1H, s), 7.70 (1H, d); ESIMS m/z 372 (M+H).

Example 25

Preparation of 2-oxo-3-benzyl-4-methyl-7-(2-aminoimidazol-1-yl-methyl)-1H-benzopyrane

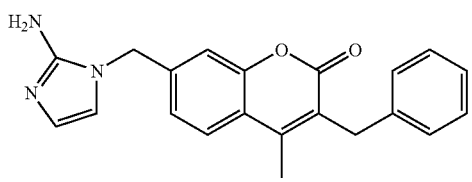

Step 1

Sodium borohydride (20.8 mg) is added to the solution of C-7 formyl coumarin (139 mg, Example 24, step 1) and amino acetaldehyde diethyl acetal (0.29 mL, 2 mmol) in a mixture of MeOH (2 mL) and THF (3 mL) at room temperature. A spoon of $MgSO_4$ is added and the reaction mixture is stirred for 24 hours. Solid is filtered out and washed with MeOH. The filtrate is concentrated under reduced pressure. The residue is re-dissolved in EtOAc and washed with water and brine and dried over $MgSO_4$. Purification of the residue after evaporation of the solvents affords the amine intermediate (144 mg).

Step 2

The above obtained amine intermediate (134-mg, 0.34 mmol) is treated with cyanamide (144 mg, 3.4 mmol) in the mixed solvents of acetic acid (0.2 mL) and water (0.8 mL). The reaction mixture is heated at 80° C. overnight. The solvents are evaporated under reduced pressure. The residue is partitioned between acetone and ether. The precipitate is filtered out and purified over preparative TLC ($CH_2Cl_2$:MeOH, 85:15) to afford the title compound as acetic acid-salt (41 mg). $^1$H NMR ($CD_3OD$) δ2.40 (3H, s), 4.02 (2H, s), 5.19 (2H, s), 6.82 (2H, d), 7.10-7.30 (7H, m), 7.79 (1H, d); ESIMS m/z 346 (M+H).

Example 26

The compounds in table V are prepared according to the indicated examples.

TABLE V

Compounds of formula (I) wherein $R_3$ is benzyl and $R_4$ is methyl. In addition, for simplicity, $R_3$ is referred to as phenylmethylene in the structure and (by inference) the table that follows, as the examples defined in the table have phenylmenthylene as $R_3$.

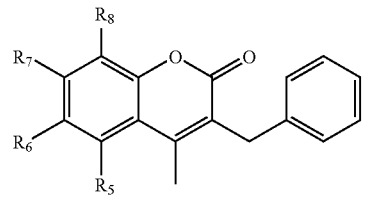

(V)

| Number of Examples | $R_7$ | $R_5, R_6, R_8$ | Physico-chemical Data (m/z, M + H) | Process of Examples |
|---|---|---|---|---|
| 26-1 | CHO | $R_5 = R_6 = R_8 = H$ | 279 | 24 |
| 26-2 | $HOCH_2CH_2$ | $R_5 = R_6 = R_8 = H$ | 313 | 24 |
| 26-3 | Et | $R_5 = R_6 = R_8 = H$ | 297 | 23 |
| 26-4 | $CH_3(OH)CH$ | $R_5 = R_6 = R_8 = H$ | 313 | 24 |
| 26-5 | $Me_2NCOO(CH_2)_2$ | $R_5 = R_6 = R_8 = H$ | 384 | 24 |
| 26-6 | Vinyl | $R_5 = R_6 = R_8 = H$ | 277 | 23 |
| 26-7 | $Me_2NCOOCH_2$ | $R_5 = R_6 = R_8 = H$ | 352 | 24 |
| 26-8 | $MeNHCH_2$ | $R_5 = R_6 = R_8 = H$ | 294 | 24 |
| 26-9 | $MeOCON(Me)CH_2$ | $R_5 = R_6 = R_8 = H$ | 352 | 24 |
| 26-10 | $EtOCON(Me)CH_2$ | $R_5 = R_6 = R_8 = H$ | 366 | 24 |
| 26-11 | $CH_3CF_2$ | $R_5 = R_6 = R_8 = H$ | 315 | 24 |
| 26-12 | $ClCH_2$ | $R_5 = R_6 = R_8 = H$ | 298 | 24 |
| 26-13 | $(EtO)_2P(O)OCH_2$ | $R_5 = R_6 = R_8 = H$ | 217 | 24 |
| 26-14 | $(EtO)_2P(O)CH_2$ | $R_5 = R_6 = R_8 = H$ | 401 | 24 |
| 26-15 | 1-(2-$NH_2$—imidazolyl)$CH_2$ | $R_5 = R_6 = R_8 = H$ | 346 | 24 |
| 26-16 | 1-(2-$NH_2$—imidazolyl)$CH_2$ | $R_6 = Cl$, $R_5 = R_8 = H$ | 381 | 24 |
| 26-17 | m-Pyridinyl | $R_5 = R_6 = R_8 = H$ | 328 | 24 |
| 26-18 | 2-(N-Methyl-benzoimidazolyl) | $R_5 = R_6 = R_8 = H$ | 381 | 24 |
| 26-19 | $CH_3CO$ | $R_6 = Cl$, $R_5 = R_8 = H$ | 327 | 24 |
| 26-20 | 2-(5-Cl-thiophene)-CH(OH)— | $R_5 = R_6 = R_8 = H$ | 397 | 24 |
| 26-21 | 2-Benzofuranyl-CH(OH) | $R_5 = R_6 = R_8 = H$ | 397 | 24 |
| 26-22 | 3-Thiophenyl-CH(OH)— | $R_5 = R_6 = R_8 = H$ | 363 | 24 |
| 26-23 | CNCH(OH) | $R_5 = R_6 = R_8 = H$ | 306 | 24 |
| 26-24 | CNCH(F)— | $R_5 = R_6 = R_8 = H$ | 308 | 24 |
| 26-25 | $NH_2COCO$— | $R_5 = R_6 = R_8 = H$ | 322 | 24 |
| 26-26 | $NH_2COCF_2$— | $R_5 = R_6 = R_8 = H$ | 344 | 24 |
| 26-27 | $Me_2NCOCH(F)$— | $R_5 = R_6 = R_8 = H$ | 354 | 24 |
| 26-28 | $Me_2NCOCF_2$ | $R_5 = R_6 = R_8 = H$ | 372 | 24 |
| 26-29 | $(HO)_2OPCF_2$— | $R_5 = R_6 = R_8 = H$ | 379(M − H) | 24 |
| 26-30 | 2-(N-Methylimidazoyl)-$S(O)CH_2$ | $R_5 = R_6 = R_8 = H$ | 428 | 25 |

Modification of the preceding embodiments is within the scope of the skilled artisan in formulation, given the guidance of the specification light of the state of the art.

All references described herein are hereby incorporated by reference.

While particular embodiments of this invention have been described, it will be obvious to those skilled in the art that various changes and modifications of this invention can be made without departing from the spirit and scope of the invention. It is intended to cover, in the appended claims, all such modifications that are within the scope of this invention.

We claim:

1. A compound of formula D:

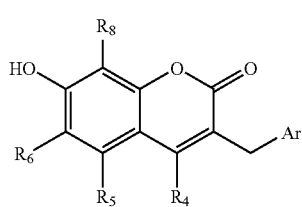

(D)

wherein,
Ar is substituted phenyl;
$R_1$ is hydrogen, hydroxy, C1 to C4 alkyl, phenyl, C1 to C2 haloalkyl, or halo;
$R_2$ is hydrogen, C1 to C5 alkyl, phenyl, or substituted phenyl,
wherein $R_1$ and $R_2$ together form an alkylene ring or a heteroalkylene ring; $R_4$ is hydrogen,
C1 to C4 alkyl,
C1 to C4 alkyl substituted with phenyl, heteroaryl, hydroxy, methoxy, or methylthio,
C1 to C2 haloalkyl (other than chloroalkyl),
benzyl,
substituted phenyl methylene,
phenyl or substituted phenyl or heteroaryl, wherein in any six membered heteroaryl, heteroatoms consist of one or two nitrogen atoms, and wherein in any five membered heteroaryl the heteroatoms consist of one to three of O, N, or S, and wherein substitution on phenyl or heteroaryl is with halo, phenyl, or C1 or C2 alkyl;
$R_5$ is hydrogen, halo, or C1 to C3 alkoxy, or $OCONR_1R_2$;
$R_6$ is hydrogen, halo, hydroxy, C1 to C4 alkoxy, C1 to C4 alkyl, cyano, nitro, or formyl; and
$R_8$ is hydrogen, halo, C1 to C4 alkyl, or formyl.

2. A compound of formula E:

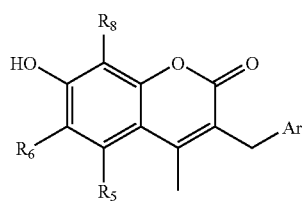

(E)

wherein,
Ar is substituted phenyl;
$R_5$ is hydrogen;
$R_6$ is hydrogen, halo, hydroxy, C1 to C4 alkoxy, C1 to C4 alkyl, cyano, nitro, or formyl; and
$R_8$ is hydrogen, halo, C1 to C4 alkyl, or formyl.

* * * * *

UNITED STATES PATENT AND TRADEMARK OFFICE
CERTIFICATE OF CORRECTION

PATENT NO. : 7,709,664 B2
APPLICATION NO. : 11/225940
DATED : May 4, 2010
INVENTOR(S) : Jie Fei Cheng Page 1 of 1

It is certified that error appears in the above-identified patent and that said Letters Patent is hereby corrected as shown below:

In column 44, line 4 claim 1, delete "phenyl" and insert --phenyl,--.

Signed and Sealed this

Seventeenth Day of August, 2010

David J. Kappos
*Director of the United States Patent and Trademark Office*